(12) United States Patent
Kino

(10) Patent No.: US 10,704,036 B2
(45) Date of Patent: Jul. 7, 2020

(54) PROTEIN HAVING SYNTHETIC ACTIVITY FOR IMIDAZOLE DIPEPTID AND PRODUCTION METHOD OF IMIDAZOLE DIPEPTIDE

(71) Applicant: TOKAI BUSSAN CO., LTD., Chiyoda-ku, Tokyo (JP)

(72) Inventor: Kuniki Kino, Tokyo (JP)

(73) Assignee: TOKAI BUSSAN CO., LTD., Tokyo (JP)

( * ) Notice: Subject to any disclaimer, the term of this patent is extended or adjusted under 35 U.S.C. 154(b) by 83 days.

(21) Appl. No.: 15/854,921

(22) Filed: Dec. 27, 2017

(65) Prior Publication Data
US 2018/0179511 A1    Jun. 28, 2018

(30) Foreign Application Priority Data

Dec. 27, 2016 (JP) ................................. 2016-252275
Aug. 30, 2017 (JP) ................................. 2017-165715

(51) Int. Cl.
| | |
|---|---|
| *C12N 9/00* | (2006.01) |
| *C12N 15/00* | (2006.01) |
| *A61K 38/03* | (2006.01) |
| *C12P 21/00* | (2006.01) |
| *C12P 21/02* | (2006.01) |
| *C07K 5/078* | (2006.01) |
| *C07K 5/02* | (2006.01) |

(52) U.S. Cl.
CPC ............ *C12N 9/93* (2013.01); *C07K 5/06147* (2013.01); *C12P 21/02* (2013.01); *C12Y 603/02028* (2013.01); *C07K 5/0202* (2013.01)

(58) Field of Classification Search
CPC .......... C12P 21/00; C12N 9/93; G02B 21/362
See application file for complete search history.

(56) References Cited

PUBLICATIONS

Tsuda et al., Biochemistry, 53, 2650-2660-2014.*
Tabata et al., J. Bacteriol., 187(15), 5195-5202, 2005.*
Song et al., Biological functions of histidine-dipeptides and metabolic syndrome, Nutrition Research and Practice, 2014, pp. 3-10.
Bellia et al., Carnosinases, Their Substrates and Diseases, Molecules, 2014, pp. 2299-2329.
Boldyrev et al., Physiology and Pathophysiology of Carnosine, American Physiological Society, 2013, pp. 1803-1845.
Ausubel et al., Current Protocols in Molecular Biologyedit, 1987.
Ausubel et al., Current protocols in molecular biology, 1987, vols. 2 to 6, John Wiley & Sons, Inc., USA.

* cited by examiner

*Primary Examiner* — Maryam Monshipouri
(74) *Attorney, Agent, or Firm* — Global IP Counselors, LLP

(57) ABSTRACT

The present invention provides L-amino acid α-ligase represented by sequence number 1 (SEQ ID NO. 1), which is a mutant protein including substitution of at least 1-3 amino acid residues of amino acid sequence of protein YwfE, with the substitution being at least one of an asparagine (N) residue of the 108th place from the N terminal being substituted with at least one of an alanine (A) residue, a glutamic acid (E) residue and a glutamine (Q) residue, an isoleucine (I) residue of the 112th place from the N terminal being substituted with a valine (V) residue, and a histidine (H) residue of the 378th place from the N terminal being substituted with at least one of a lysine (K) residue or an arginine (R) residue.

13 Claims, 4 Drawing Sheets
Specification includes a Sequence Listing.

PROTEIN HAVING SYNTHETIC ACTIVITY FOR IMIDAZOLE DIPEPTID AND PRODUCTION METHOD OF IMIDAZOLE DIPEPTIDE

CROSS-REFERENCE TO RELATED APPLICATIONS

This application claims priority to Japanese Patent Application No. 2016-252275 filed on Dec. 27, 2016 and Japanese Patent Application No. 2017-165715 filed on Aug. 30, 2017. The entire disclosures of Japanese Patent Application No. 2016-252275 and Japanese Patent Application No. 2017-165715 are hereby incorporated herein by reference.

BACKGROUND

Technical Field

The present invention relates to protein having synthetic activity for imidazole dipeptide such as carnosine, anserine and balenine, and also relates to a production method of imidazole dipeptide.

Related Art

Imidazole dipeptide is a general term of peptide to which an amino acid residue including an imidazole group is joined. The imidazole dipeptide includes dipeptide including histidine residues such as carnosine (β-alanyl-L-histidine), anserine (β-alanyl-3-methyl-L-histidine) and balenine (Nα-β-alanyl-1-methyl-L-histidine) or its derivatives.

The dipeptide is contained a lot in breast meat of birds flying a long distance or in muscle of marine life making an excursion of long distance such as tuna, bonito or whale.

It is known that the imidazole dipeptide has antifatigue-effect, active-oxygen-elimination-ability, blood-pressure-descent effect, anti-inflammatory-effect and uric-acid-level-descent-effect, and the imidazole dipeptide extracted from muscle of domestic animals such as cocks is used as a supplement (for example, see Song B. et al., Nutr Res Pract. 2014, 8:3-10; Bellia F. et al., Molecules 2014, 19:2299-2329; and Boldyrev A. A. et al., Physiol Rev. 2013, 93:1803-45). However, a simple, easy and low-cost production method of carnosine, anserine and balenine have not yet been established.

SUMMARY

The object of the present invention is to provide imidazole dipeptide which is simple, easy and low-cost.

According to the present invention, a protein which can produce imidazole dipeptide such as carnosine, anserine and balenine in high efficiency is provided. According to the present invention, a host cell in which the gene encoding the protein is installed is also provided. According to the present invention, a production method of the imidazole peptide using the protein is also provided.

The inventor paid his attention to the fact that L-amino acid α-ligase conjugates with a hydrolysis reaction of the ATP, and L-amino acid α-ligase is an enzyme catalyzing peptide synthesis by forming α-peptide bond as a substrate with no protected amino acid. That is, the inventor produced a mutant enzyme by applying site-specific mutagenesis to protein YwfE having L-amino acid α-ligase activity derived from Bacillus, and evaluated the imidazole dipeptide synthetic activity. As a result, the inventor discovered that the mutant enzyme in which a particular part is replaced with particular amino acid residue has strong imidazole peptide synthetic activity, particularly, carnosine synthetic activity, anserine synthetic activity and/or balenine synthetic activity. Then the inventor accomplished the present invention.

Specifically, the present invention provides L-amino acid α-ligase represented by sequence number 1 (SEQ ID NO. 1), which is a mutant protein including substitution of at least 1-3 amino acid residues of amino acid sequence of protein YwfE, with the substitution being at least one of an asparagine (N) residue of the 108th place from the N terminal being substituted with at least one of an alanine (A) residue, a glutamic acid (E) residue and a glutamine (Q) residue, an isoleucine (I) residue of the 112th place from the N terminal being substituted with a valine (V) residue, and a histidine (H) residue of the 378th place from the N terminal being substituted with at least one of a lysine (K) residue and an arginine (R) residue.

The mutant protein of the present invention may have L-amino acid α-ligase activity.

The mutant protein of the present invention is at least one of (i), (ii) and (iii).

(i) Protein having amino acid sequence of SEQ ID NOS. 2-16.

(ii) Protein having homology of 80% or more to amino acid sequence of SEQ ID NOS. 2-16 and having L-amino acid α-ligase activity.

(iii) Protein having amino acid sequence of SEQ ID NOS. 2-16 in which at least one of deletion, substitution, insertion and addition occurs to at least one amino acid residue and having L-amino acid α-ligase activity.

In the present invention, the L-amino acid α-ligase activity may be selected from at least one of carnosine synthetic activity, anserine synthetic activity and balenine synthetic activity.

In a case where the L-amino acid α-ligase activity is carnosine synthetic activity, the mutant protein of the present invention is at least one of (i), (ii) and (iii).

(i) Protein having amino acid sequence of SEQ ID NOS. 2-4, 6, 7, 9, 10, 12-16.

(ii) Protein having homology of 80% or more to amino acid sequence of SEQ ID NOS. 2-4, 6, 7, 9, 10, 12-16 and having carnosine synthetic activity.

(iii) Protein having amino acid sequence of SEQ ID NOS. 2-4, 6, 7, 9, 10, 12-16 in which at least one of deletion, substitution, insertion and addition occurs to at least one amino acid residue and having carnosine synthetic activity.

In a case where the L-amino acid α-ligase activity is anserine synthetic activity, the mutant protein of the present invention is at least one of (i), (ii) or (iii).

(i) Protein having amino acid sequence of SEQ ID NOS. 2, 3, 5, 6, 8-16.

(ii) Protein having homology of 80% or more to amino acid sequence of SEQ ID NOS. 2, 3, 5, 6, 8-16 and having anserine synthetic activity.

(iii) Protein having amino acid sequence of SEQ ID NOS. 2, 3, 5, 6, 8-16 in which at least one of deletion, substitution, insertion and addition occurs to at least one amino acid residue and having anserine synthetic activity.

In a case where the L-amino acid α-ligase activity is balenine synthetic activity, the mutant protein of the present invention is at least one of (i), (ii) or (iii).

(i) Protein having amino acid sequence of SEQ ID NOS. 6, 7, 11, 14-16.

(ii) Protein having homology of 80% or more to amino acid sequence of SEQ ID NOS. 6, 7, 11, 14-16 and having balenine synthetic activity.

(iii) Protein having amino acid sequence of SEQ ID NOS. 6, 7, 11, 14-16 in which at least one of deletion, substitution, insertion and addition occurs to at least one amino acid residue and having balenine synthetic activity.

The present invention provides a nucleic acid encoding mutant protein of the present invention.

The present invention provides a vector in which polynucleotide including nucleic acid of the present invention is inserted.

The present invention provides a host cell including at least one kind of vector of the present invention.

The present invention provides a production method of dipeptide using mutant protein of the present invention.

In the production method of the present invention, the protein of the present invention may be used with an activity inhibitor of peptidase.

In the production method of the present invention, the host cell of the present invention may be used.

In the production method of the present invention, the host cell may be a deficient cell of peptidase.

In the production method of the present invention, the peptidase may be peptidase D.

In the production method of the present invention, the deficient cell may be JW0227 strain.

In the production method of the present invention, the dipeptide may be imidazole dipeptide.

In the production method of the present invention, the imidazole dipeptide may be carnosine, anserine and/or balenine.

According to the present invention, by providing protein producing imidazole dipeptide in high efficiency and a host cell containing the protein, it can provide imidazole dipeptide including carnosine, anserine and balenine simply, easily and at low cost. Also by using a peptidase deficient cell as a host cell, it can produce imidazole dipeptide, particularly carnosine, in high efficiency.

BRIEF DESCRIPTION OF THE DRAWINGS

Referring now to the attached drawings which form a part of this original disclosure.

DETAILED DESCRIPTION OF EXEMPLARY EMBODIMENTS

1. Protein of the Present Invention

Figure 1:
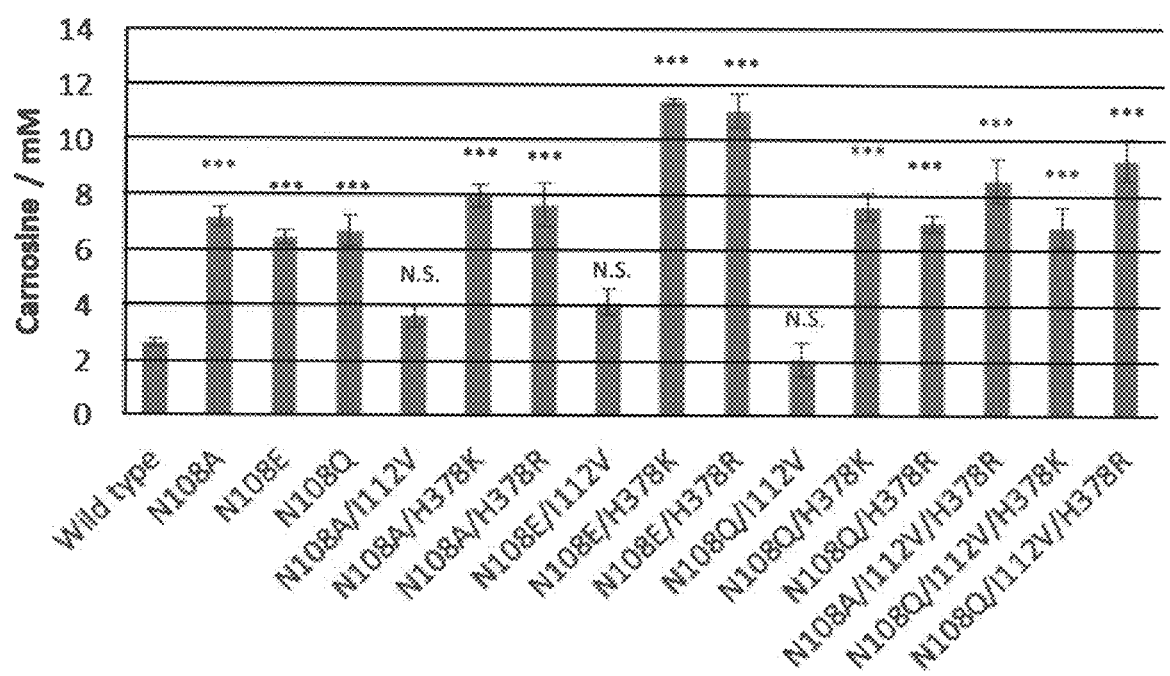
FIG. 1 shows carnosine synthetic activity evaluation results of mutant enzyme including wild type YwfE and site specific mutation type YwfE, in which * indicates that "p value" is less than 0.05,  indicates that "p value" is less than 0.01, and * indicates that "p value" is less than 0.001.

One of the embodiments of the present invention is mutant enzyme of protein YwfE having L-amino acid α-ligase activity, whose origin is *Bacillus subtilis* which is *Bacillus* bacteria.

In this specification, the L-amino acid α-ligase activity is imidazole dipeptide synthetic activity, and imidazole dipeptide includes carnosine, anserine and balenine.

The mutant enzyme is the enzyme in which the ligase activity to the amino acid is improved, that is, an asparagine (N) residue of the 108th place from the N terminal of wild type YwfE is substituted with an alanine (A) residue, a glutamic acid (E) residue or a glutamine (Q) residue, alternatively or in addition, an isoleucine (I) residue of the 112th place is substituted with a valine (V) residue, and/or, a histidine (H) residue of the 378th place is substituted with a lysine (K) residue or a arginine (R) residue, and the N-terminal side substrate is β-alanine, and the C-terminal side substrate is histidine or its derivative.

In this specification, sequence of protein is described in amino acid notation using three characters or one character that is the usage well known to those skilled in the art. The amino acid is L body unless otherwise specified in the specification. Also, when it represents mutant protein in the specification, it is indicated by a conventional method well known to those skilled in the art. That is, one character notation representing amino acid in which mutation of the wild type protein is installed, a number representing a mutation position, and one character notation representing mutated amino acid are used.

Specifically, the mutant protein of the present invention is L-amino acid α-ligase represented by sequence number 1 (SEQ ID NO. 1): that is, a mutant protein including substitution of at least 1-3 amino acid residues of amino acid sequence of protein YwfE having ligase activity, and an asparagine (N) residue of the 108th place from the N terminal is substituted with an alanine (A) residue, a glutamic acid (E) residue or a glutamine (Q) residue, alternatively, in addition, an isoleucine (I) residue of the 112th place is substituted with a valine (V) residue, and/or, a histidine (H) residue of the 378th place is substituted with a lysine (K) residue or a arginine (R) residue.

That is, the mutant protein of the present invention is exemplified by following (i)-(iii).

(i) Protein having amino acid sequence of SEQ ID NOS. 2-16.

(ii) Protein having homology of 80% or more, preferably 85% or more, more preferably 90% or more, most preferably 95% or more to amino acid sequence of SEQ ID NOS. 2-16 and having L-amino acid α-ligase activity.

(iii) Protein having amino acid sequence of SEQ ID NOS. 2-16, in which deletion, substitution, insertion and/or addition occurs to 1 or a plurality of amino acid residues, and having L-amino acid α-ligase activity.

Also, the L-amino acid α-ligase activity is preferably dipeptide synthetic activity, more preferably, carnosine (L-Carnosine) synthetic activity, anserine (L-Anserine) synthetic activity and/or balenine (L-Balenine) synthetic activity.

Chemical formula 1

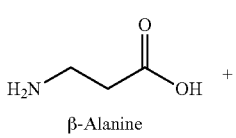

β-Alanine

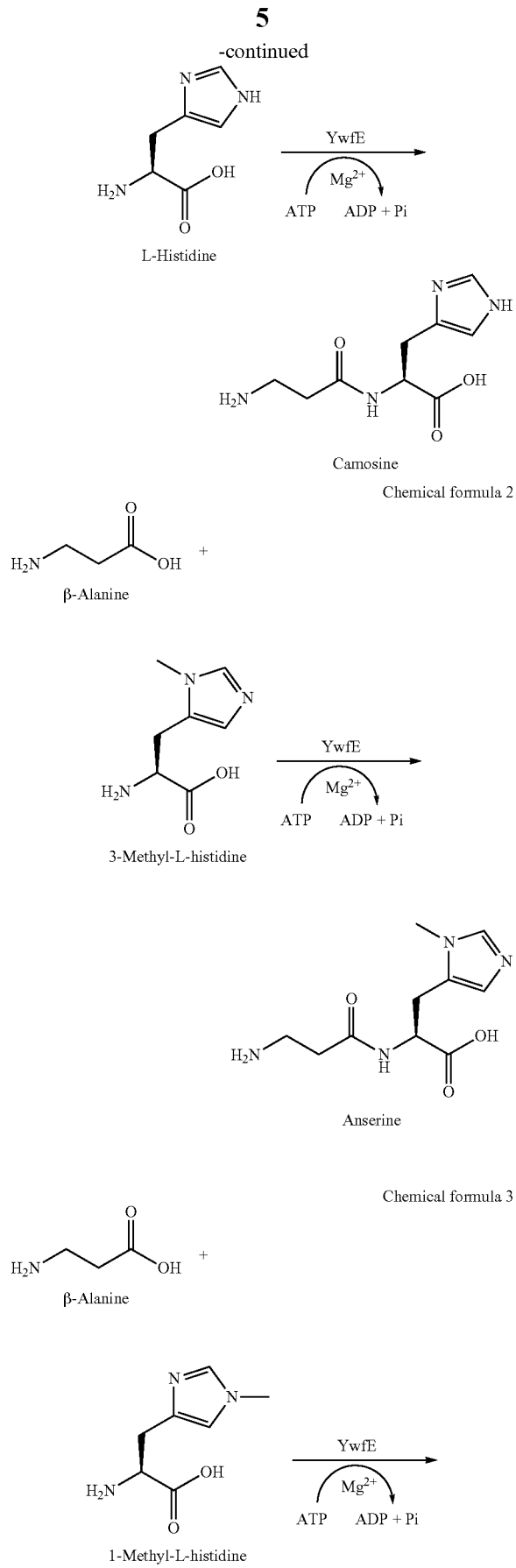

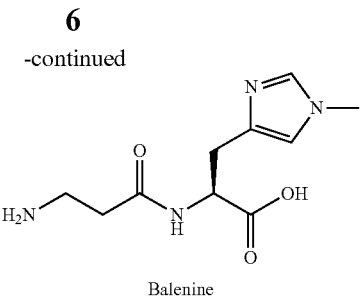

Balenine

In this specification, "having L-amino acid α-ligase activity" means that having more than equivalence L-amino acid α-ligase activity of wild type YwfE, and when the activity of the protein of the present invention is compared with wild type YwfE in the same condition other than the difference in the protein itself, it means the protein showing improved L-amino acid α-ligase activity in comparison with L-amino acid α-ligase activity of wild type YwfE.

In this specification, evaluation of L-amino acid α-ligase activity, particularly, dipeptide synthetic activity is performed by the following method. First, a test protein and an amino acid as a substrate are put into a buffering water solution of pH 5-11 (for example) including ATP, and it is incubated at 20-50 degrees Celsius (for example) for 2-150 hours (for example) to, produce dipeptide by the incubation. At least one of the followings is selected for an index, which includes increase in the quantity or density of the dipeptide, reduction in the quantity or density of the amino acid as the substrate, reduction in the quantity or density of ATP, increase in the quantity or density of ADP, or increase in the quantity or density of inorganic phosphoric acid. Then, for example, it is measured using high performance liquid chromatography, and compared with the dipeptide synthetic activity of wild type YwfE in the same condition except the test protein itself.

Also, it is described as follows in this specification. [Protein in which the amino acid residue corresponding to $Z_1$ residue ($Z_1$) of Yth from the N terminal of SEQ ID NO. X is replaced with $Z_2$ residue ($Z_2$)" ("X" and "Y" represent integers 1 or more, "Z1" and "Z2" represent any amino acid, "($Z_1$)" and "($Z_2$)" represent each amino acid in one character).]

In the above description, when it aligned to give the highest sequence homology score in amino acid sequence and SEQ ID NO. X of the protein, the protein has amino acid sequence in which $Z_1$ residue of Yth from the N terminal of the amino acid sequence of SEQ ID NO. X is substituted with $Z_2$ residue.

Characteristics of the protein of the present invention will be explained below in detail.

Figure 2:
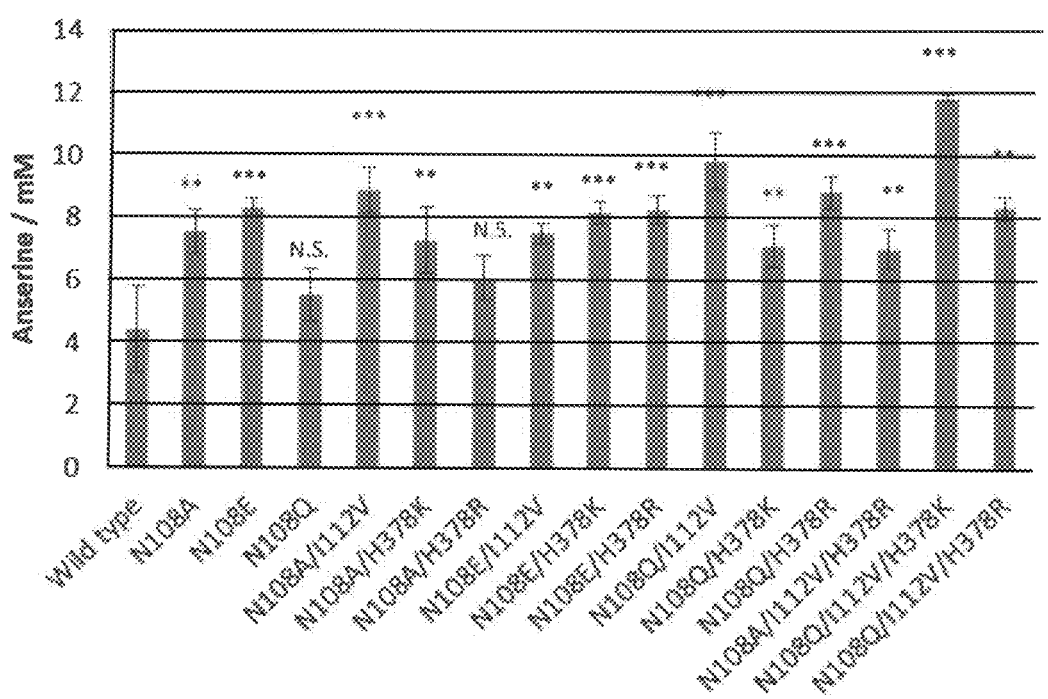
FIG. 2 shows anserine synthetic activity evaluation results of mutant enzyme including wild type YwfE and site specific mutation type YwfE, in which * indicates that "p value" is less than 0.05,  indicates that "p value" is less than 0.01, and * indicates that "p value" is less than 0.001.

As shown in FIG. 2, *Bacillus* origin wild type protein YwfE having L-amino acid α-ligase activity has synthetic activity of dipeptide in which the C terminal is L-histidine (Tabata K. et al., J. Bacteriol., 2,005,187:5195-5202). However, the wild type protein YwfE has not strong α-ligase activity in production of carnosine whose N terminal is β-alanine and C terminus is dipeptide of histidine, and anserine or balenine which are derivatives of carnosine (see FIG. 2). That is, strong carnosine synthetic activity, strong anserine synthetic activity and strong balenine synthetic activity are brought by making the wild type protein of YwfE to a mutant.

In the expression of L-amino acid α-ligase activity of the protein of the present invention, stronger activity is observed in a case applying β-Ala as the N-terminal substrate and applying His as the C-terminal substrate, compared with a case of applying Ala and Gly as the N-terminal substrate and applying His as the C-terminal substrate. The protein of the present invention has selective strong activity to synthesis of carnosine, or anserine and balenine which are derivatives of carnosine. Optimal mutant enzymes to the synthesis of carnosine, and anserine and balenine which are derivatives of carnosine do not necessarily coincide with each other.

Based on the characteristics obtained from a single amino acid mutant protein of the present invention, the mutant enzyme in which two or three amino acid residues are replaced is designed in the present invention, and a protein of a double mutant enzyme or a triple mutant enzyme is provided by the present invention.

The examples of the double mutant enzyme or triple mutant enzyme include mutation of N108A, N108E or N108Q, mutation of I112V, mutation of H378K or H378R, and combination of such mutation. In most of these double mutant enzymes or triple mutant enzymes, carnosine synthetic activity, anserine synthetic activity and balenine synthetic activity are improved compared to each activity of wild type YwfE, but all activity may not be always improved equally.

That is, when the L-amino acid α-ligase activity of the protein of the present invention is carnosine synthetic activity, it is preferable that the protein includes substitution of the asparagine (N) residue of the 108th place from the N-terminal of SEQ ID NO. 1 by an amino acid residue selected from an alanine (A) residue, a glutamic acid (E) residue or a glutamine (Q) residue; substitution of the isoleucine (I) residue of the 112th place from the N-terminal of SEQ ID NO. 1 by a valine (V) residue; and/or, substitution of the histidine (H) residue of the 378th place of SEQ ID NO. 1 by a lysine (K) residue or an arginine (R) residue.

When the L-amino acid α-ligase activity of the protein of the present invention is anserine synthetic activity, it is preferable that the protein includes substitution of the asparagine (N) residue of the 108th place from the N-terminal of SEQ ID NO. 1 by an amino acid residue selected from an alanine (A) residue, a glutamic acid (E) residue or a glutamine (Q) residue; substitution of the isoleucine (I) residue of the 112th place from the N-terminal of SEQ ID NO. 1 by a valine (V) residue; and/or, substitution of the histidine (H) residue of the 378th place of SEQ ID NO. 1 by a lysine (K) residue or an arginine (R) residue.

In addition, when the L-amino acid α-ligase activity of the protein of the present invention is balenine synthetic activity, it is preferable that the protein includes substitution of the asparagine (N) residue of the 108th place from the N-terminal of SEQ ID NO. 1 by an amino acid residue selected from an alanine (A) residue or a glutamine (Q) residue; substitution of the isoleucine (I) residue of the 112th place from the N-terminal of SEQ ID NO. 1 by a valine (V) residue; and/or, substitution of the histidine (H) residue of the 378th place of SEQ ID NO. 1 by a lysine (K) residue or an arginine (R) residue.

A single mutant enzyme of the mutation protein of YwfE is prepared, for example, as follows. A Site-Directed Mutagenesis is performed by conventional PCR (polymerase chain reaction) well known to those skilled in the art using a template DNA represented by SEQ ID NO. 17, and using a primer having nucleic acid sequence represented by SEQ ID NOS. 33-44 to produce a vector (nucleic acid insertion vector) in which polynucleotide including a nucleic acid encoding the protein of SEQ ID NOS. 2-16 of the present invention as described below is inserted, in addition, to produce a host cell including the nucleic acid insertion vector of the present invention in which the nucleic acid insertion vector is installed (it is referred to as "transformed cell" hereinafter), and the host cell including the transformed cell in proper nutrient medium is cultured, and protein prepared by the transformants is isolated and purified by using the isolation and purification method such as salt precipitation, gel chromatography, or gel electrophoresis For example, DNA which is used as a template is provided by the following method. Using a probe designed from partial sequence of polynucleotide sequence of SEQ ID NO. 17, polynucleotide of SEQ ID NO. 17 of a full length is prepared by a southern hybridization method for chromosome DNA of the microbe which codes YwfE protein of Bacillus subtilis 168 or relation protein.

Also, a double mutant enzyme can be prepared, for example, by the following method. A nucleic acid insertion vector in which regiospecific mutation of the single mutant used in production of the single mutant enzyme is installed is prepared. Using the nucleic acid insertion vector as a template and using a primer having nucleic acid sequence represented by SEQ ID NOS. 33-44, a Site-Directed Mutagenesis by conventional PCR well known to those skilled in the art is performed to prepare a host cell including the nucleic acid vector in which double mutation is installed, the host cell is cultured in proper nutrient medium in the same manner as production of the single mutant enzyme, and then isolated and purified to obtain the double mutant enzyme.

In addition, a triple mutant enzyme can be prepared, for example, by the following method. A nucleic acid insertion vector in which regiospecific mutation of the double mutant used in production of the double mutant enzyme is installed is prepared. Using the nucleic acid insertion vector as a template and using a primer having nucleic acid sequence represented by SEQ ID NOS. 33-44, a Site-Directed Mutagenesis by conventional PCR well known to those skilled in the art is performed to prepare a host cell including the nucleic acid vector in which triple mutation is installed, the host cell is cultured in proper nutrient medium in the same manner as production of the double mutant enzyme, and then isolated and purified to obtain the triple mutant enzyme.

The protein of the present invention is used as an enzyme to produce carnosine, anserine or balenine. That is, the transformed cell in which nucleic acid encoding amino acid sequence of the protein is installed is prepared, and carnosine, anserine and/or balenine is produced by culturing the transformed cell.

2. A Nucleic Acid of the Present Invention

Another embodiment of the present invention is a nucleic acid encoding protein of following (i)-(iii).

(i) Protein having amino acid sequence of SEQ ID NOS. 2-16.

(ii) Protein having homology of 80% or more, preferably 85% or more, more preferably 90% or more, most preferably 95% or more to amino acid sequence of SEQ ID NOS. 2-16 and having L-amino acid α-ligase activity.

(iii) Protein having amino acid sequence of SEQ ID NOS. 2-16, in which deletion, substitution, insertion and/or addition occurs to 1 or a plurality of amino acid residues, and having L-amino acid α-ligase activity.

The nucleic acid is prepared by using a primer designed based on a polynucleotide sequence of SEQ ID NO. 17, and by introducing Site-Directed Mutagenesis using the Site-Directed Mutagenesis method in which chromosome DNA of the microbe encoding YwfE protein of Bacillus subtilis 168 or the relation protein is used as a mold.

For specific means to install objective mutation into template gene, various Site-Directed Mutagenesis methods well-known to a person having ordinary skill in the art can be used basically based on a reproduction reaction due to PCR amplification in which polynucleotide of SEQ ID NO. 17 is used as a mold DNA, or various DNA polymerase. For example, the Site-Directed Mutagenesis method can be performed by any technique such as PCR method or annealing method (Muramatsu et al. "fourth edition revision new genetic engineering handbook", Yohdosha, p. 82-88). As necessary, it can use a kit for various commercial Site-Directed Mutagenesis, such as, QuickChange II Site-Directed Mutagenesis Kit (Stratagene Corporation, U.S.A.), QuickChange Multi Site-Directed Mutagenesis Kit (Agilent technology company, U.S.A.).

Mold DNA including the YwfE gene can be prepared by extracting genomic DNA, or extracting RNA and synthesizing cDNA by reverse transcription, from bacteria producing YwfE protein with a fixed method. The bacteria producing YwfE protein are reported in plants and animals as well as the bacteria including Bacillus bacteria such as hay bacillus (*Bacillus subtilis*), *clostridium*, acid *thermus* genus bacteria. Among those, *bacillus* bacteria such as hay *bacillus* (*Bacillus subtilis*) is preferable and is easily available to a person having ordinary skilled in the art. For example, KSM-S237 strain (accession number FERM BP-7875) of *bacillus* sp, KSM-64 strain (accession number FERM BP-2886) of *bacillus* sp, and KSM-635 strain (accession number FERM BP-1485) of *bacillus* sp are deposited in the incorporated administrative agency, National Institute of Advanced Industrial Science and Technology, patent biology deposit center (chuo 6th 1-1-1 Tsukubashi-higashi, Ibaraki, Japan), with written jointly the accession number.

Preparation of genomic DNA from these *bacillus* bacteria, for example, can be performed using a method described in Pitcher et al., Lett. Appl. Microbiol., 1989, 8: p. 151-156. Mold DNA including YwfE gene may be prepared in the form of cDNA or in which a DNA fragment including the YwfE gene cut from genomic DNA is inserted in any vector.

Most common installation of the regiospecific mutation to the YwfE gene can be performed using a mutation primer including the nucleotidic mutation to be installed. Such a mutation primer should be designed to anneal in the area including a nucleotide sequence encoding an amino acid residue for the substitution in the YwfE gene, and to include a base sequence having a nucleotide sequence (codon) encoding the amino acid residue after the substitution instead of a nucleotide sequence (codon) encoding the amino acid residue for the substitution.

The nucleic acid prepared by these methods is available to prepare the vector which produces the protein of the present invention in a host cell, to produce a host cell in which the vector is installed, namely, a transformed cell, and to produce the protein of the present invention.

3. A Vector (Nucleic Acid Insertion Vector) in which Polynucleotide Including the Nucleic Acid Encoding the Protein of the Present Invention is Inserted Another embodiment of the present invention is a nucleic acid insertion vector including a gene encoding the protein of the present invention and proper expression sequence. The expression vector to produce these recombinant DNAs is available commercially. By obtaining and using these vectors, the nucleic acid insertion vector of the present invention, and the host cell including the nucleic acid insertion vector, that is, the transformed cell, can be produced.

When *Escherichia coli* is used for the host cell, for example, vectors include pColdI (made by Takara bio), pCDF-1b, pRSF-1b (both made by Nova Gen Corporation), pMAL-c2x (made by New England biolabs), pGEX-4T-1 (made by GE health care bioscience), pTrcHis (made by Invitro Gen), pSE280 (made by Invitro Gen), pGEMEX-1 (made by Promega), pQE-30 (made by Kia gene), pET-3 (made by Nova Gen), pBluescript II SK (+), pBluescript II KS (−) (made by Stratagene), pTrS30 [prepared from *Escherichia coli* JM109/pTrS30 (FERM BP-5407)].

For a promoter when the vectors are used, any kind of promoter can be used if it functions in host cells such as *Escherichia coli*. For example, promoters coming from *Escherichia coli* or bacteriophages can be used such as a trp promoter (Ptrp), a lac promoter (Plac), a PL promoter, a PR promoter, a PSE promoter. When a microbe belonging to *Bacillus* as parent root is used, an SPO1 promoter, an SPO2 promoter, a penP promoter functioning in *Bacillus subtilis* can be used. Also promoters which are designed artificially can be used such as a promoter in which a couple of Ptrp is connected directly, a tac promoter, a lacT7 promoter, a led promoter.

When a vector is used to produce the protein of the present invention, an expression vector in particular is useful. As for the expression vector, it should be a vector expressing a protein in a test tube, in colon *bacillus*, in a cultured cell or in a creature individual. For example, if the expression occurs in a test tube, a pBEST vector (a product made by Promega company) is preferable. If the expression occurs in colon *bacillus*, a pET vector (made by Invitro Gen) is preferable. If the expression occurs in a cultured cell, a pME18S-FL3 vector (GenBank Accession No. AB009864) is preferable. If the expression occurs in a creature individual, a pME18S vector (Mol Cell Biol. 8: 466-472 (1988)) is preferable. Common methods can be used for the insertion of DNA of the present invention to a vector. For example, it can be conducted by the ligase reaction using the restriction enzyme site (Current protocols in Molecular Biology Edited by Ausubel et al. (1987) Publish. John Wiley & Sons. Section 11.4-11.11).

4. Host Cell of the Present Invention

Another embodiment of the present invention is a transformed host cell. This transformed host cell is provided by inserting the nucleic acid insertion vector into a host cell to express the protein of the present invention. As a reagent to install a nucleic acid insertion vector in a host cell, various reagents are commercially available and one of these can be obtained and used for production of the transformed cell.

The host cell is selected from fungal cell, fungus cell, algal cell, animal cell, insect cell, bacteria cell, plant cell and old bacteria cell, and it is preferably bacteria cell. The bacteria cell includes *Escherichia* cell, *Bacillus* cell, *Lactobacillus* cell, *Rhodococcus* cell, *Pseudomonas* cell, *Aspergillus* cell, but is not limited to these. From a point of view producing imidazole dipeptide products (e.g., carnosine, anserine, balenine) in high efficiency, the host cell, is preferably a degrading enzyme of imidazole dipeptide, in particular, a deficient cell of peptidase D.

Specifically, as an example of the host cell in which the vector of the present invention is installed, it can preferably use microbe belonging to the followings. *Escherichia* genus bacteria, such as, Colon *bacillus*, Actinomycetes genus bacteria, *Bacillus* genus bacteria, *Serratia* genus bacteria, *Pseudomonas* genus bacteria, *Corynebacterium* genus bacteria, *Brevibacterium* genus bacteria, *Rhodococcus* genus bacteria, *Lactobacillus* genus bacteria, *Streptomyces* genus bacteria, *Thermus* genus bacteria, *Streptococcus* genus bacteria, *Saccharomyces* genus yeast, *Pichia* genus yeast, *Kluyveromyces* genus yeast, *Candida* genus yeast, *Schizosaccharomyces* genus yeast, *Debaryomyces* genus yeast, *Yarrowia* genus yeast, *Cryptococcus* genus yeast, *Xanthophyllomyces* genus yeast, *Mortierella* genus filamentous fungus, *Fusarium* genus filamentous fungus, *Schizochytrium* genus microbe, *Thraustochytrium* genus microbe. The preferred host cell is Colon *bacillus*, *Actinomyces*, Bacteria belonging to *Pseudomonas* genus, and Yeast which belongs to *Saccharomyces*.

As the host cell of the present invention, the followings can be used specifically. *Escherichia coli, Bacillus subtilis, Bacillus brevis, Bacillus stearothermophilus, Serratia marcescens, Pseudomonas putida, Pseudomonas aeruginosa, Corynebacterium glutamicum, Brevibacterium flavum, Brevibacterium lactofermentum, Rhodococcus erythropolis, Thermus thermophilus, Streptococcus lactis, Lactobacillus casei, Streptomyces lividans, Saccharomyces cerevisiae, Saccharomyces bayanus, Pichia pastoris, Kluyveromyces lactis, Candida utilis, Candida glabrata, Schizosaccharomyces pombe, Debaryomyces hansenii, Yarrowia lypolitica, Cryptococcus curvatus, Xanthophyllomyces dendrorhous, Aspergillus nigar, Aspergillus oryzae, Mortierella ramanniana, Mortierella bainieri, Mortierella alpina, Cunninghamella elegans, Fusarium fujikuroi, Schizochytrium limacium, Thraustochytrium aureum.*

An insertion method of the nucleic acid insertion vector to the host cell includes the following methods. Calcium phosphate transfection, DEAE-dextran mediated transfection, Polybrene mediated transfection, Protoplast fusion, Liposome mediated transfection (lipofection), Zygosis, Natural transformation, Electroporation and other methods well known to those skilled in the art. Also, because the transfection reagents are available commercially, the installation of the expression vector to host cell can be carried out by using these.

[Reference: Current protocols in molecular biology. 3 vols. Edited by Ausubel F. M. et al., John Wiley & Son, Inc., Current Protocols.]

5. Production Method of Dipeptide of the Present Invention

Using the protein or the transformed cell of the present invention, the dipeptide of the present invention is prepared as follows. That is, the amino acid which is production raw materials and becomes a substrate of the protein of the present invention is incubated in an ATP coexisted buffer solution, or cultured in a nutrient medium for cell cultures, and then isolated from the buffer solution or the medium to produce the desired dipeptide. The amino acid as the raw materials includes a combination of one or two kinds of amino acid selected from the following groups. L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-Aminobutyricacid, L-Azaserine, L-Theanine, L-4-Hydroxyproline, L-3-Hydroxyproline, L-Ornithine, L-Citrulline, L-6-Diazo-5-oxo-norleucine, glycine (Gly), and β-alanine (β-Ala).

For the buffer solution, the example includes a phosphate buffer solution, a boric acid buffer solution, a citric acid buffer solution, an acetic acid buffer solution and a tris hydrochloric acid buffer solution, which are common to a person having ordinary skill in the art.

For a carbon ingredient included in the cell culture medium, any ingredient which serves for utilization by the host cell and transformed cell can be used. Specifically, the following ingredients can be used. Glucose, Fructose, Sucrose, Molasses having these, Starch, Carbohydrates such as starch hydrolysate, Organic acid such as acetic acid or propionic acids, Alcohol such as ethanol or propanol.

For a nitrogen source, the followings can be used for example. Ammonia, Ammonium chloride, Ammonium sulfate, Acetic acid ammonium, Ammonium salt of inorganic acid or organic acid such as ammonium phosphate, Other nitrogen-containing compounds, and Peptone, Meat extract essence, Yeast extract, Corn steep liquor, Casein hydrolysate, Soybean cake and soybean cake hydrolysate, Various fermentation bacteria, and digest of the fermentation bacteria.

For inorganic salt, the followings can be used. Primary potassium phosphate, Secondary potassium phosphate, Magnesium phosphate, Magnesium sulfate, Sodium chloride, Ferrous sulfate, Manganese sulfate, Copper sulfate, Calcium carbonate. In addition, Peptone, Meat extract essence, Yeast extract, Corn steep liquor, Casamino acids and Various vitamins such as the biotin can be added to the nutrient medium.

Cultivation is usually carried out under aerobic conditions such as ventilation stirring, shaking or the like. There is no limitation of the cultivation temperature in particular as long as the host cell or transformed cell can grow. Also, As for pH in the middle of the cultivation, there is no limitation of such pH in particular as long as the host cell or transformed cell can grow. Adjustment of the pH in the middle of the cultivation is performed by adding acid or alkali.

In the above described cultivation, Carnosine, Anserine and/or Balenine is produced in high efficiency by using the activity inhibitor of the peptidase, particularly peptidase D when the protein of the present invention is used, or by using a deficient cell of the peptidase particularly JW0227 strain as the host cell when the host cell is used, to restrain resolution of a imidazole dipeptide product (e.g., carnosine, anserine, balenine) by the peptidase.

The desired enzyme can be collected from a culture using a well-known collection method using the activity of the desired enzyme as index. The desired enzyme does not need to be purified until it becomes uniform, and it should be purified to a certain refinement degree depending on applications.

Specific manufacturing methods of carnosine, anserine and balenine as the dipeptide will be explained below.

(1) A Production Method of Carnosine by Incubating the Protein of the Present Invention in a Buffer Solution Including an Amino Acid as a Substrate Carnosine is produced by performing condensation reaction of β-alanine and L-histidine as a substrate using the protein of the present invention as a catalyst. Therefore, the protein of the present invention is added to a buffer solution including β-alanine and L-histidine, incubation is performed for a predetermined period of time, and produced carnosine is isolated and purified to produce the desired carnosine.

In the producing process, 0.01-100 mg, preferably 0.1-10 mg of the protein of the present invention is added to per 1 mg of an amino acid as a substrate. In the producing process, the amino acid as the substrate is added at the beginning or in the middle of reaction to an aqueous medium so that the concentration becomes 0.1-100 g/L, preferably 0.2-40 g/L. In the producing process, ATP can be used as an energy source and the concentration of the ATP is 0.5-1 mol/L.

The production reaction by incubation in an aqueous medium, is performed under conditions of pH 5-11, preferably pH 6-10, 20-50 degrees Celsius, preferably 25-45 degrees Celsius, and for 2-72 hours, preferably 6-36 hours.

Isolation and purification of carnosine which is generated and accumulated in the buffer solution is performed with a conventional method for those skilled in the art using activated carbon or ion-exchange resin, or extraction using an organic solvent, crystallization, thin layer chromatography, high-performance liquid chromatography, and the like.

(2) A Production Method of Carnosine Using the Transformed Cell of the Present Invention Carnosine is produced by performing condensation reaction of β-alanine and L-histidine as a substrate using the protein of the present invention as a catalyst. Therefore, the transformed cell of the present invention is cultivated in a nutrient medium for cell cultures including β-alanine and L-histidine, and produced carnosine is isolated and purified to produce and acquire desired carnosine.

In the producing process, 0.01-100 mg, preferably 0.1-10 mg of the protein of the present invention is added to per 1 mg of an amino acid as a substrate. In the producing process, the quantity of β-alanine and L-histidine to be added is usually each 0.5-100 g/L, preferably 2-50 g/L. In the cell nutrient medium including these amino acids, the transformed cell of the present invention is cultivated with a conventional method well known to those skilled in the art.

Cultivation is usually carried out under aerobic conditions such as shaking cultivation or deep aeration stirring cultivation. As for the cultivation temperature, 15-40 degrees Celsius is preferable, and the cultivation time is usually for 5 hours-7 days. The pH during the cultivation is held to 3.0-9.0. The adjustment of pH is carried out using an inorganic or organic acid, an alkaline solution, urea, calcium carbonate, ammonia, and the like.

Isolation and purification of carnosine which is generated and accumulated in the buffer solution is performed with a conventional method for those skilled in the art using activated carbon or ion-exchange resin, or extraction using an organic solvent, crystallization, thin layer chromatography, high-performance liquid chromatography, and the like.

(3) A Production Method of Anserine by Incubating the Protein of the Present Invention in a Buffer Solution Including an Amino Acid as a Substrate Anserine is a dipeptide in which β-alanine and 3-methyl-L-histidine are bonded by peptide bond. Therefore, when anserine using the protein of the present invention is produced, incubation is performed in the same conditions as "(1) A production method of carnosine by incubating the protein of the present invention in a buffer solution including an amino acid as a substrate" except for using 3-methyl-L-histidine instead of L-histidine which is one of the substrates, and produced anserine is isolated and purified.

(4) A Production Method of Anserine Using the Transformed Cell of the Present Invention Anserine is a dipeptide in which β-alanine and 3-methyl-L-histidine are bonded by peptide bond. Therefore, when anserine is produced using the protein of the present invention, "(2) A production method of carnosine using the transformed cell of the present invention" is carried out in the same conditions except for using 3-methyl-L-histidine instead of L-histidine which is one of the substrates, and then anserine is produced and obtained.

(5) A Production Method of Balenine by Incubating the Protein of the Present Invention in a Buffer Solution Including an Amino Acid as a Substrate Balenine is a dipeptide in which β-alanine and 1-methyl-L-histidine are bonded by peptide bond. Therefore, when balenine is produced using the protein of the present invention, incubation is performed in the same conditions as "(1) A production method of carnosine by incubating the protein of the present invention in a buffer solution including an amino acid as a substrate" except for using 1-methyl-L-histidine instead of L-histidine which is one of the substrates, and produced balenine is isolated and purified.

(6) A Production Method of Balenine Using the Transformed Cell of the Present Invention Balenine is a dipeptide in which β-alanine and 1-methyl-L-histidine are bonded by peptide bond. Therefore, when balenine is produced using the protein of the present invention, i "(2) A production method of carnosine using the transformed cell of the present invention" is carried out in the same conditions as "(2) A production method of carnosine using the transformed cell of the present invention" except for using 1-methyl-L-histidine instead of L-histidine which is one of the substrates, and then balenine is produced and obtained.

As for the documents mentioned in this specification, the entire disclosures are incorporated in this specification by reference. The embodiments described herein exemplifies the present invention, and it should not be interpreted as limiting the range of the present invention.

Embodiment 1

In the following embodiments, preparation of polynucleotide (DNA, mRNA), PCR, sequencing, transformation, expression of a protein, purification of a protein, and HPLC analysis can be carried out using a conventional method well known to those skilled in the art. For example, refer to Sambrook, J. and Russell, D. W., Molecular Cloning A Laboratory Manual 4th Edition, Cold Spring Harbor Laboratory Press (2012).

Installation of Site-Specific Mutagenesis to YwfE

Choosing a pET vector in which YwfE gene (SEQ ID NO. 11) is incorporated as a mold, objective mutation is installed using Quick Change Site-Directed Mutagenesis (Strategene, U.S.A.) according to the instructions of the manufacturer. PCR reaction is carried out in reaction conditions shown in Table 1 (composition) and Table 2 (PCR cycle). KOD-Plus-Neo-DNA polymerase (Toyobo Co., Ltd., Osaka) is used in the PCR reaction. Using a primer (SEQ ID NOS. 33-44), a vector in which site-specific mutagenesis of N108A, N108E or N108Q is installed is obtained. Note that, the vector to N108A represents polynucleotide (SEQ ID NO. 18), and this polynucleotide encodes YwfE protein in which an asparagine (N) residue of 108th from an N terminal of the YwfE protein is replaced with an alanine (A) residue. The vector to N108E represents polynucleotide (SEQ ID NO. 19), and this polynucleotide encodes YwfE protein in which an asparagine (N) residue of 108th from an N terminal of the YwfE protein is replaced with a glutamic acid (E) residue. The vector to N108Q represents polynucleotide (SEQ ID NO. 20), and this polynucleotide encodes YwfE protein in which an asparagine (N) residue of 108th from an N terminal of the YwfE protein is replaced with a glutamine (Q) residue.

TABLE 1

| | |
|---|---|
| KOD-Plus-Neo buffer solution | 5 μL |
| 2 mM dNTP | 5 μL |
| 25 mM MgSO$_4$ | 3 μL |
| 10 mM forward primer | 1 μL |
| 10 mM reverse primer | 1 μL |
| Template plasmid (50 μg/mL) | 1 μL |
| KOD-Plus-Neo-DNA Polymerase | 1 μL |
| Sterile MilliQ | 33 μL |
| Total | 50 μL |

TABLE 2

| Step | Temperature/° C. | Time/second |
|---|---|---|
| Thermal denaturation before the cycle | 94 | 120 |
| Thermal denaturation | 98 | 10 |
| Annealing, Tensile | 68 | 210 |
| The last tensile reaction | 68 | 60 |
| Preservation | 4 | ∞ |

Number of cycles of PCR reaction (Thermal denaturation/Annealing, Tensile): 40 cycles After the PCR reaction, the obtained PCR product is analyzed using DNA sequencer (Applied Biosystems, Life Technologies Japan Co., Ltd., Tokyo), and it is confirmed whether site-specific mutagenesis was installed.

DpnI site of the vector extracted from colon *bacillus* is methylated by Dam methylase; however, DpnI site of the PCR product is not methylated. It is thus possible to distinguish the mold vector and the PCR product by using this fact.

In summary, to remove the mold vector included in the reaction liquid after PCR, the purified PCR product is processed in DpnI at 37 degrees Celsius for 2 hours. A restriction enzyme reaction is carried out in conditions shown in Table 3.

TABLE 3

| | |
|---|---|
| DNA (PCR product) | 50 μg |
| 10 X TA buffer solution | 5 μL |
| Dpn I (1000 U) | 1 μL |
| MilliQ | 44 μL |

After the DpnI processing, the Site-Directed Mutagenesis vector is purified by phenol chloroform processing and ethanol precipitation, and then dissolved in a TE buffer solution of pH 8.0.

Transformation of Colon *Bacillus* JM109 by Site-Directed Mutagenesis Vector.

A competent cell of colon *bacillus* JM109 and the site-directed mutagenesis vector are treated by heat at 42 degrees Celsius together. Subsequently, an SOC nutrient medium is added for cultivation inoculated into an LB agar nutrient medium containing kanamycin 50 μg/mL, and cultivated at 37 degrees Celsius overnight.

One colony is selected from colonies which grew up and suspended into an LB medium 3 mL containing kanamycin to cultivate at 37 degrees Celsius for 5 hours. After the incubation, the site-directed mutagenesis vector extracted from the transformed cell by an alkali SDS method. The extracted site-directed mutagenesis vector is purified by phenol chloroform processing and ethanol precipitation, and then dissolved in a TE buffer solution (pH 8.0).

Preparation of Purified Enzyme
Transformation of Colon *Bacillus* BL21 by Site-Directed Mutagenesis Vector Colon *bacillus* BL21 is transformed by a heat shock method using the purified site-directed mutagenesis vector. A competent cell of colon *bacillus* BL21 and the site-directed mutagenesis vector are treated by heat at 42 degrees Celsius together. Subsequently, an SOC nutrient medium is added for cultivation, inoculated into an LB agar nutrient medium containing kanamycin 50 μg/mL, and cultivated at 37 degrees Celsius overnight. The colon *bacillus* which formed a colony here is assumed as the YwfE expression transformed cell.

Expression Induction by IPTG

One colony is selected from colonies of the transformed cell expressing YwfE which grew up, and suspended into an LB media 3 mL containing kanamycin for pre-cultivation at 37 degrees Celsius for 5 hours in a test tube. Then 2 mL of the pre-cultivated fluid is added to an LB media 200 mL containing kanamycin in an Erlenmeyer flask with a 500 mL baffle. Next, main cultivation is performed at 37 degrees Celsius, 120 rpm for 2 hours, and then 100 mM IPTG 200 μL is added. Overnight cultivation is performed at 25 degrees Celsius, 120 rpm after IPTG addition.

After the overnight cultivation, centrifugal separation with 5,000 Xg, 10 minutes is performed to collect cell bodies, the cell body pellet is suspended in a 100 mM Tris-HCl buffer solution (pH 8.0) to wash the cell body. This operation is repeated two times and the nutrient medium ingredient is removed. After washing, the cell body pellet is cryopreserved at −80 degrees Celsius.

Purification of Enzyme

A protein is extracted by adding BugBuster (Bug Buster™ Protein Extraction Reagent, Merck KGaA company, Germany) and lysozyme to the cell body pellet which was defrosted. The pulverized cell suspension is separated into precipitation (insoluble fraction) and supernatant (cell-free extract) by centrifugal separation. The cell-free extract is applied using HisGraviTrap (GE Health Care company, U.S.A.) according to the instructions of the manufacturer. The eluted solution is desalted using PD-10 column (GE Health Care company) according to the instructions of the manufacturer. The purifed enzyme is stored at −80 degrees Celsius until it is used in the following experiments.

Measurement of Concentration of the Purified Enzyme

After color reaction using Coomassie Brilliant Blue, the concentration of the purified enzyme is measured by a microplate reader MODEL550 (Bio-Rad company, U.S.A.). The concentration of the purified enzyme is determined from measurements of absorbance of 595 nm by a calibration curve method.

Double Mutant Enzyme

Double mutant enzymes are prepared and the carnosine synthetic activity is evaluated. The double mutant enzymes are the combination of mutation of N108A, N108E or N108Q and mutation of I112V, H378K or H378R, and the examples of the double mutant enzymes are as follows.

N108A/I112V (SEQ ID NO. 5)
N108A/H378K (SEQ ID NO. 6)
N108A/H378R (SEQ ID NO. 7)
N108E/I112V (SEQ ID NO. 8)
N108E/H378K (SEQ ID NO. 9)
N108E/H378R (SEQ ID NO. 10)
N108Q/I112V (SEQ ID NO. 11)
N108Q/H378K (SEQ ID NO. 12)
N108Q/H378R (SEQ ID NO. 13)

In summary, in the same manner as the installation of the above site-specific mutagenesis, a vector having site-specific mutagenesis of N108A, N108E or N108Q is used as a template, and a primer (SEQ ID NOS. 39 and 40) of I112V, a primer (SEQ ID NOS. 41 and 42) of H378K or a primer (SEQ ID NOS. 43 and 44) of H378R, are used. The site-specific mutagenesis (I112V, H378K or H378R) is introduced, and then a vector having double site-specific mutagenesis is obtained. Subsequently, in the same manner as in the above, the purified double site specific mutation type YwfE (SEQ ID NOS. 5-13) is obtained.

Triple Mutant Enzyme

Triple mutant enzymes are prepared and the carnosine synthetic activity is evaluated. The triple mutant enzymes are the combination of mutation of N108A/I112V or N108Q/I112V and mutation of H378K or H378R, that is, N108A/I112V/H378K (SEQ ID NO. 14), N108Q/I112V/H378K (SEQ ID NO. 15), and N108Q/I112V/H378R (SEQ ID NO. 16). In summary, in the same manner as the installation of the above site-specific mutagenesis, a vector having site-specific mutagenesis of N108A/I112V or N108Q/I112V is used as a template. A primer (SEQ ID NOS. 41 and 42) of H378K, or a primer (SEQ ID NOS. 43 and 44) of H378R is used. The site-specific mutagenesis (H378K or H378R) is introduced, and then a vector having triple site-specific mutagenesis is obtained. Subsequently, in the same manner as in the above, the purified triple site specific mutation type YwfE (SEQ ID NOS. 14-16) is obtained.

Carnosine Synthetic Activity Evaluation (HPLC Analysis)

Commercially available carnosine (Sigma-Aldrich, U.S.A.) is used as a sample. As for the quantity of synthesis of peptide, HPLC analysis is carried out using the $N^{\alpha}$-(5-fluoro-2, 4-dinitrophenyl)-L-alanineamide (FDAA) derivatization method, and the quantity is determined by the calibration curve method. The HPLC analysis was carried out according to the fixed rule in the conditions shown in Table 4 (eluent composition) and Table 5 (gradient program).

<Analysis Condition>
Apparatus: HITACHIL-7000 series (Hitachi, Ltd., Tokyo)
Column: WH-C18A (4*150 mm) (Hitachi High Technologies Co., Ltd., Tokyo)
Sample injection quantity: 10 μL
Speed: 0.5 mL/min
Column temperature: 40 degrees Celsius
UV detection wavelength: 340 nm

TABLE 4

Composition of eluent in HPLC analysis

| Ingredient | Eluent A (mL) | Eluent B (mL) | Eluent C (mL) |
|---|---|---|---|
| Acetonitrile | 50 | 350 | 600 |
| Methanol | 50 | 50 | — |
| Tetrahydrofuran | — | — | 200 |
| 50 mM $KH_2PO_4$ (pH 2.7) | 900 | 600 | — |
| MilliQ | — | — | 200 |
| Total volume | 1000 | 1000 | 1000 |

TABLE 5

Condition of gradient of the eluent in HPLC analysis

| Time (minute) | Eluent A (%) | Eluent B (%) | Eluent C (%) |
|---|---|---|---|
| 0 | 80 | 20 | 0 |
| 10 | 80 | 20 | 0 |
| 35 | 0 | 100 | 0 |
| 35.1 | 0 | 0 | 100 |
| 37.1 | 0 | 0 | 100 |
| 37.2 | 80 | 20 | 0 |
| 50 | 80 | 20 | 0 |

Carnosine synthesis is carried out at 30 degrees Celsius for 20 hours in a reaction liquid of the composition shown in Table 6. As the enzyme, the followings are used. Wild-type enzyme (SEQ ID NO. 1)
N108A (SEQ ID NO. 2), N108E (SEQ ID NO. 3) and N108Q (SEQ ID NO. 4) as the single mutant enzyme
N108A/I112V (SEQ ID NO. 5), N108A/H378K (SEQ ID NO. 6), N108A/H378R (SEQ ID NO. 7), N108E/I112V (SEQ ID NO. 8), N108E/H378K (SEQ ID NO. 9), N108E/14378R (SEQ ID NO. 10), N108Q/I112V (SEQ ID NO. 11), N108Q/H378K (SEQ ID NO. 12) and N108Q/H378R (SEQ ID NO. 13) as the double mutant enzyme
N108A/I112V/H378R (SEQ ID NO. 14), N108Q/I112V/H378K (SEQ ID NO. 15) and
N108Q/I112V/H378R (SEQ ID NO. 16) as the triple mutant enzyme After the reaction end, to evaluate the carnosine synthesis, analysis by HPLC is performed in the same manner as in the above.

Regarding statistical test, EZR (http://www.jichi.ac.jp/saitama-sct/SaitamaHP.files/statmed.htm) is used as statistics test software. Using the concentration of carnosine produced by the wild-type enzyme as a comparison target, post hoc analysis (each group n=3) is performed to the concentration of carnosine produced by each mutant enzyme, with P value 0.05 being as a level of significance, by one-way analysis of variance (ANOVA) and assay of Dunnett. Also, the following statistical analysis of anserine synthetic activity evaluation and balenine synthetic activity evaluation is carried out in a similar manner.

TABLE 6

Composition of the reaction liquid

| Composition | Density |
|---|---|
| β-alanine | 12.5 mM |
| L-histidine | 12.5 mM |
| ATP | 12.5 mM |
| $MgSO_4$ | 12.5 mM |
| Enzyme (Wild type or Mutant type) | 0.25 mg/mL |

Total 300 μL/Tris-HCL buffer solution (pH 9.0)

Results

FIG. 1 shows carnosine the concentration of carnosine by carnosine synthesis of the following enzymes.
Wild-type enzyme (SEQ ID NO. 1)
N108A (SEQ ID NO. 2), N108E (SEQ ID NO. 3) and N108Q (SEQ ID NO. 4) as the single mutant enzyme
N108A/I112V (SEQ ID NO. 5), N108A/H378K (SEQ ID NO. 6), N108A/H378R (SEQ ID NO. 7), N108E/I112V (SEQ ID NO. 8), N108E/H378K (SEQ ID NO. 9), N108E/H378R (SEQ ID NO. 10), N108Q/I112V (SEQ ID NO. 11), N108Q/H378K (SEQ ID NO. 12) and N108Q/H378R (SEQ ID NO. 13) as the double mutant enzyme
N108A/I112V/H378R (SEQ ID NO. 14), N108Q/I112V/H378K (SEQ ID NO. 15) and
N108Q/I112V/H378R (SEQ ID NO. 16) as the triple mutant enzyme In every mutant enzyme except N108A/I112V (SEQ ID NO. 5), N108E/I112V (SEQ ID NO. 8) and N108Q/I112V (SEQ ID NO. 11), it is observed that the carnosine synthetic activity has increased with statistical significance compared to the wild type. Also, N108E/H378K (SEQ ID NO. 9) was the highest in the carnosine synthetic activity, and the yield was 91.4%.

Embodiment 2

Evaluation of Anserine Synthetic Activity

In the same manner as the carnosine synthetic activity evaluation of Embodiment 1, anserine synthetic activity of the following 15 kinds of mutant enzymes is evaluated by comparing to the activity of the wildtype.
(N108A, N108E, N108Q, N108A/I112V, N108A/H378K, N108A/H378R, N108E/I112V, N108E/H378K, N108E/H378R, N108Q/I112V, N108Q/H378K, N108Q/H378R, N108A/I112V/H378R, N108Q/I112V/H378K and N108Q/I112V/H378R).

In summary, anserine synthesis is carried out at 30 degrees Celsius for 20 hours in a reaction liquid of the composition shown in Table 7. After the reaction, the anserine synthetic activity of each mutant enzyme is evaluated by determining the quantity of the anserine concentration by HPLC in the same manner as in Embodiment 1. Commercially available anserine (Wako JunYaku Industries Co., Ltd., Osaka) is used as a sample of anserine.

TABLE 7

Composition of the reaction liquid

| Composition | Density |
| --- | --- |
| β-alanine | 25 mM |
| 3-methyl-L-histidine | 25 mM |
| ATP | 12.5 mM |
| MgSO$_4$ | 12.5 mM |
| Enzyme | 0.50 mg/mL |

Total 300 μL/100 mM Tris-HCL buffer solution (pH 9.0)

Results

Results of measurement are shown in FIG. 2. In every mutant enzyme except N108Q (SEQ ID NO. 4) and N108A/H378R (SEQ ID NO. 7), it is observed that the anserine synthetic activity has increased with statistical significance compared to the wild type. Also, N108Q/I112V/H378K (SEQ ID NO. 15) was the highest in the anserine synthetic activity, and the yield was 94.7%.

Embodiment 3

Evaluation of Balenine Synthetic Activity

In the same manner as the carnosine synthetic activity evaluation of Embodiment 1, balenine synthetic activity of the following 15 kinds of mutant enzymes is evaluated by comparing to the activity of the wildtype.
(N108A, N108E, N108Q, N108A/I112V, N108A/H378K, N108A/H378R, N108E/I112V, N108E/H378K, N108E/H378R, N108Q/I112V, N108Q/H378K, N108Q/H378R, N108A/I112V/H378R, N108Q/I112V/H378K and N108Q/I112V/H378R).

In summary, balenine synthesis is carried out at 30 degrees Celsius for 20 hours in a reaction liquid of the composition shown in Table 8. After the reaction, the balenine synthetic activity of each mutant enzyme is evaluated by determining the quantity of the balenine concentration by HPLC in the same manner as in Embodiment 1. Commercially available balenine (Hamari Chemicals Co., Ltd., Osaka) is used as a sample of balenine.

TABLE 8

Composition of reaction mixture

| Composition | Concentration |
| --- | --- |
| β-alanine | 12.5 mM |
| 1-methyl-L-histidine | 12.5 mM |
| ATP | 12.5 mM |
| MgSO$_4$ | 12.5 mM |
| enzyme | 0.25 mg/mL |

Total 300 μL/100 Tris-HCl buffer (pH 9.0)

Results

Figure 3:
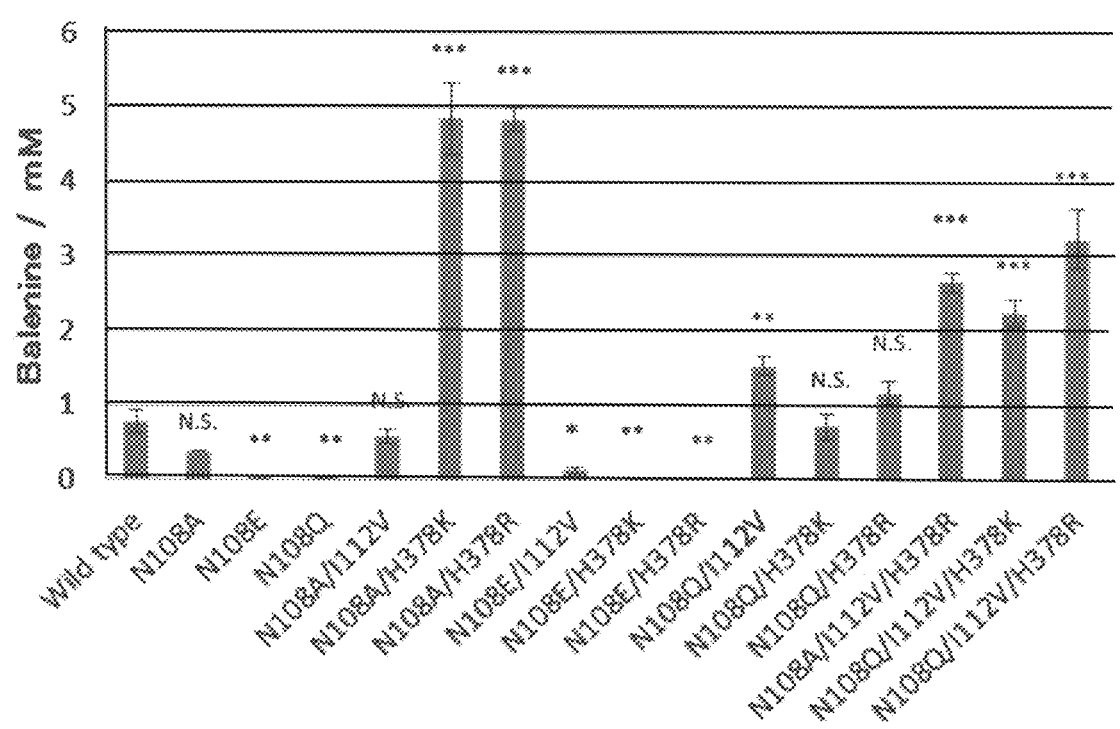
FIG. 3 shows balenine synthetic activity evaluation results of mutant enzyme including wild type YwfE and site specific mutation type YwfE, in which * indicates that "p value" is less than 0.05,  indicates that "p value" is less than 0.01, and * indicates that "p value" is less than 0.001.

Results of measurement are shown in FIG. 3. In 6 kinds of mutant enzymes (N108A/H378K, N108A/H378R, N108Q/I112V, N108A/I112V/H378R, N108Q/I112V/H378K and N108Q/I112V/H378R), it is observed that the balenine synthetic activity has increased with statistical significance compared to the wild type. Also, N108A/H378K (SEQ ID NO. 6) was the highest in the balenine synthetic activity, and the yield was 38.8%.

From the above-mentioned results, regarding 4 kinds of mutant enzymes (N108A/H378K (SEQ ID NO. 6), N108A/I112V/H378R (SEQ ID NO. 14), N108Q/I112V/H378K (SEQ ID NO. 15) and N108Q/I112V/H378R (SEQ ID NO. 16)), it is observed that the carnosine synthetic activity, the anserine synthetic activity and the balenine synthetic activity have increased with statistical significance compared to the wild type.

Embodiment 4

Influence of Peptidase in Carnosine Synthesis

Peptidase D (pepD) recognizes dipeptide (Xaa-His) having any amino acid (Xaa) of the N-terminal side and histidine (His) of the C-terminal side, and resolves the dipeptide (J. Gen. Microbiol. 172, 2337-2343 (1986)). Therefore, in the production method using a cell, it was assumed that the resolution of carnosine could be prevented by using the cell body which has suffered loss of pepD. Accordingly, using Escherichia coli JM101 strain and JW0227 strain, comparison and evaluation of the resolution activity of carnosine were performed. The JW0227 strain was obtained by causing the JM101 strain to lose a gene of pepD which is one kind of peptidase.

TABLE 9

| Strain | Genotype |
| --- | --- |
| JM101 | supE, thi, Δ(lac-proAB)/F[traD36, proAB$^+$, lac I$^q$, lacZΔM15] |

The carnosine resolution due to bacterial reaction is carried out at 30 degrees Celsius for 0-20 hours in a reaction liquid of the composition shown in Table 10. The solution after the reaction is processed at 90 degrees Celsius for 10 minutes and the reaction is stopped. The supernatant was analyzed by HPLC after centrifugal separation for 20 minutes. The carnosine residual ratio was calculated after 20-hour reaction with the carnosine concentration of 0 hour being 100%.

TABLE 10

|  | Concentration |
|---|---|
| Carnosine | 2.0 mM |
| Whole cell | 100 mg/ml |
| Tris-HCl (pH 9.0) | 100 mM |
| Total | 300 μL |

Results

Figure 4:
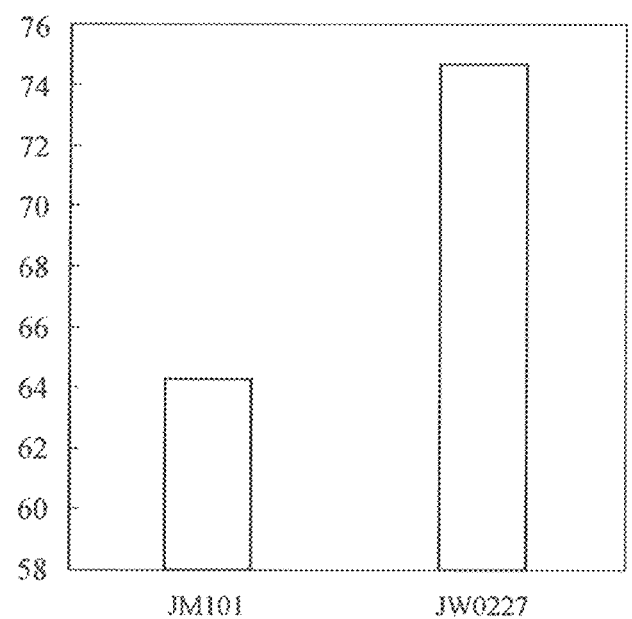
FIG. 4 shows evaluation results of influence of peptidase in carnosine synthesis.

FIG. 4 shows the carnosine residual ratio when JM101 strain and JW0227 strain are used as a host cell, respectively. The carnosine residual ratio was 64.2% in JM101 strain, and 74.7% in JW0227 strain. From this, by using the peptidase deficient strain, the resolution of the produced carnosine is controlled, which allows carnosine to be produced in high efficiency. Also, it is indicated that anserine and balenine could be produced in high efficiency by using the peptidase deficient strain.

By providing the protein, particularly carnosine, anserine and/or balenine which produce imidazole dipeptide in high efficiency, the vector which includes a nucleic acid encoding the protein, and the host cell which contains the protein, it becomes possible to provide imidazole dipeptide simply, easily and at low cost. Also by using a peptidase deficient cell as a host cell, imidazole dipeptide, particularly carnosine, can be produced in high efficiency.

Sequence Listing

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

---

What is claimed is:

1. A mutant protein of L-amino acid α-ligase represented by wild type SEQ ID NO. 1, the mutant protein including a substitution of at least 1-3 amino acid residues of amino acid sequence of protein YwfE, with the substitution being at least one of:
   an asparagine (N) residue of a 108th place from an N terminal of the mutant protein being substituted with at least one of an alanine (A) residue, a glutamic acid (E) residue and a glutamine (Q) residue,
   an isoleucine (I) residue of a 112th place from the N terminal of the mutant protein being substituted with a valine (V) residue, and
   a histidine (H) residue of a 378th place from the N terminal of the mutant protein being substituted with at least one of a lysine (K) residue and an arginine (R) residue,
   the mutant protein being a protein having an amino acid sequence selected from the group consisting of: SEQ ID NO. 2 (N108A), SEQ ID NO. 3 (N108E), SEQ ID NO. 4 (N108Q), SEQ ID NO. 5 (N108A/I112V), SEQ ID NO. 6 (N108A/H378K), SEQ ID NO. 7 (N108A/H378R), SEQ ID NO. 8 (N108E/I112V), SEQ ID NO. 9 (N108E/H378K), SEQ ID NO. 10 (N108E/H378R), SEQ ID NO. 11 (N108Q/I112V), SEQ ID NO. 12 (N108Q/H378K), SEQ ID NO. 13 (N108Q/H378R), SEQ ID NO. 14 (N108A/I112V/H378R), SEQ ID NO. 15 (N108Q/I112V/H378K) and SEQ ID NO. 16 (N108Q/I112V/H378R) the mutant having L-amino acid α-ligase activity, and the N terminal of the mutant protein being a residue located at the position 1 of the amino acid sequence.

2. The mutant protein according to claim 1, wherein the L-amino acid α-ligase activity is at least one selected from the group consisting of: carnosine synthetic ability, anserine synthetic ability and balenine synthetic ability.

3. A nucleic acid which encodes the mutant protein according to claim 1.

4. A vector in which a polynucleotide including the nucleic acid according to claim 3 is inserted.

5. A host cell which includes at least one kind of the vector according to claim 4.

6. A production method of a dipeptide using the mutant protein according to claim 1, comprising:

incubating the mutant protein according to claim 1 in a buffer solution including an amino acid as a substrate to form the dipeptide, or cultivating the mutant protein according to claim 1 in a cell culture medium including the amino acid as the substrate to form the dipeptide, and isolating the dipeptide from the buffer solution or the cell culture medium.

7. The production method of the dipeptide according to claim 6, wherein the cell culture medium further includes an activity inhibitor of peptidase.

8. A production method of a dipeptide using the host cell according to claim 5, comprising cultivating the host cell according to claim 5 in a cell culture medium including the amino acid as the substrate to form the dipeptide, and isolating the dipeptide from the cell culture medium.

9. The production method of the dipeptide according to claim 8, wherein the host cell is a deficient cell of peptidase.

10. The production method of the dipeptide according to claim 7, wherein the peptidase is peptidase D.

11. The production method of the dipeptide according to claim 9, wherein the peptidase is peptidase D.

12. The production method of the dipeptide according to claim 6, wherein the peptidase is imidazole dipeptide.

13. The production method of the dipeptide according to claim 12, wherein the imidazole dipeptide is at least one of carnosine, anserine and balenine.

* * * * *

SEQUENCE LISTING

<160> NUMBER OF SEQ ID NOS: 44

<210> SEQ ID NO 1
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (wild type)

<400> SEQUENCE: 1

```
Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140
```

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
            165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
            405                 410                 415

Ser Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln His Ala Lys Leu
    450                 455                 460

Thr Ala Lys Tyr Val Leu Pro Val
465                 470

<210> SEQ ID NO 2
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108A)

<400> SEQUENCE: 2

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

-continued

```
Phe Ile Pro Arg Pro Phe Ala Ile Thr Ala Ser His Ala Ala Leu Ile
         35                  40                  45

Glu Lys Tyr Ser Val Ala Val Ile Lys Asp Lys Tyr Phe Lys Ser
 50                  55                  60

Leu Ala Asp Phe Glu His Pro Asp Ser Ile Tyr Trp Ala His Glu Asp
 65                  70                  75                  80

His Asn Lys Pro Glu Glu Val Val Glu Gln Ile Val Lys Val Ala
                 85                  90                  95

Glu Met Phe Gly Ala Asp Ala Ile Thr Thr Asn Ala Glu Leu Phe Ile
                100                 105                 110

Ala Pro Met Ala Lys Ala Cys Glu Arg Leu Gly Leu Arg Gly Ala Gly
             115                 120                 125

Val Gln Ala Ala Glu Asn Ala Arg Asp Lys Asn Lys Met Arg Asp Ala
 130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                 165                 170                 175

Leu Lys Pro Thr Tyr Leu Ala Ser Ser Ile Gly Val Thr Leu Ile Thr
             180                 185                 190

Asp Thr Glu Thr Ala Glu Asp Glu Phe Asn Arg Val Asn Asp Tyr Leu
                 195                 200                 205

Lys Ser Ile Asn Val Pro Lys Ala Val Thr Phe Glu Ala Pro Phe Ile
210                 215                 220

Ala Glu Glu Phe Leu Gln Gly Tyr Gly Asp Trp Tyr Gln Thr Glu
225                 230                 235                 240

Gly Tyr Ser Asp Tyr Ile Ser Ile Glu Gly Ile Met Ala Asp Gly Glu
                 245                 250                 255

Tyr Phe Pro Ile Ala Ile His Asp Lys Thr Pro Gln Ile Gly Phe Thr
                 260                 265                 270

Glu Thr Ser His Ile Thr Pro Ser Ile Leu Asp Glu Glu Ala Lys Lys
             275                 280                 285

Lys Ile Val Glu Ala Ala Lys Ala Asn Glu Gly Leu Gly Leu Gln
 290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
             325                 330                 335

Asn Ile Lys Lys Val Phe Gly Leu Asp Met Ala Gln Leu Leu Leu Asp
             340                 345                 350

Val Leu Cys Phe Gly Lys Asp Ala Asp Leu Pro Asp Gly Leu Leu Asp
             355                 360                 365

Gln Glu Pro Tyr Tyr Val Ala Asp Cys His Leu Tyr Pro Gln His Phe
 370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
             405                 410                 415

Ser Phe Ser Ala Ala Ala Pro Gly Thr Ser Val Asp Leu Thr Leu Phe
             420                 425                 430

Glu Ala Phe Asn Ser Ile Ala Ala Phe Glu Leu Lys Gly Ser Asn Ser
             435                 440                 445
```

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 3
<211> LENGTH: 472
<212> TYPE: PRT
<213> ORGANISM: Bacillus subtilis

<400> SEQUENCE: 3

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Glu Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

```
Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
        370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470
```

<210> SEQ ID NO 4
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108Q)

<400> SEQUENCE: 4

```
Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Gln Glu Leu Phe Ile
            100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
        130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
```

```
                  225                 230                 235                 240
        Gly Tyr Ser Asp Tyr Ile Ser Ile Glu Gly Ile Met Ala Asp Gly Glu
                        245                 250                 255

Tyr Phe Pro Ile Ala Ile His Asp Lys Thr Pro Gln Ile Gly Phe Thr
                        260                 265                 270

Glu Thr Ser His Ile Thr Pro Ser Ile Leu Asp Glu Ala Lys Lys
                        275                 280                 285

Lys Ile Val Glu Ala Ala Lys Lys Ala Asn Glu Gly Leu Gly Leu Gln
                        290                 295                 300

Asn Cys Ala Thr His Thr Glu Ile Lys Leu Met Lys Asn Arg Glu Pro
        305                 310                 315                 320

Gly Leu Ile Glu Ser Ala Ala Arg Phe Ala Gly Trp Asn Met Ile Pro
                        325                 330                 335

Asn Ile Lys Lys Val Phe Gly Leu Asp Met Ala Gln Leu Leu Leu Asp
                        340                 345                 350

Val Leu Cys Phe Gly Lys Asp Ala Asp Leu Pro Asp Gly Leu Leu Asp
                        355                 360                 365

Gln Glu Pro Tyr Tyr Val Ala Asp Cys His Leu Tyr Pro Gln His Phe
                        370                 375                 380

Lys Gln Asn Gly Gln Ile Pro Glu Thr Ala Glu Asp Leu Val Ile Glu
        385                 390                 395                 400

Ala Ile Asp Ile Pro Asp Gly Leu Leu Lys Gly Asp Thr Glu Ile Val
                        405                 410                 415

Ser Phe Ser Ala Ala Ala Pro Gly Thr Ser Val Asp Leu Thr Leu Phe
                        420                 425                 430

Glu Ala Phe Asn Ser Ile Ala Ala Phe Glu Leu Lys Gly Ser Asn Ser
                        435                 440                 445

Gln Asp Val Ala Glu Ser Ile Arg Gln Ile Gln Gln His Ala Lys Leu
                        450                 455                 460

Thr Ala Lys Tyr Val Leu Pro Val
        465                 470

<210> SEQ ID NO 5
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108A/I112V)

<400> SEQUENCE: 5

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
                35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Ala Glu Leu Phe Val
                100                 105                 110
```

```
Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 6
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108A/H378K)

<400> SEQUENCE: 6
```

```
Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Ala Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys Lys Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415
```

```
Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 7
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108A/H378R)

<400> SEQUENCE: 7

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Ala Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300
```

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys Arg Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 8
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108E/I112V)

<400> SEQUENCE: 8

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Glu Glu Leu Phe Val
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr 180                 185                 190
Asp Thr Glu Thr Ala Glu Asp Glu Phe Asn Arg Val Asn Asp Tyr Leu
        195                 200                 205
Lys Ser Ile Asn Val Pro Lys Ala Val Thr Phe Glu Ala Pro Phe Ile
    210                 215                 220
Ala Glu Glu Phe Leu Gln Gly Glu Tyr Gly Asp Trp Tyr Gln Thr Glu
225                 230                 235                 240
Gly Tyr Ser Asp Tyr Ile Ser Ile Glu Gly Ile Met Ala Asp Gly Glu
                245                 250                 255
Tyr Phe Pro Ile Ala Ile His Asp Lys Thr Pro Gln Ile Gly Phe Thr
            260                 265                 270
Glu Thr Ser His Ile Thr Pro Ser Ile Leu Asp Glu Glu Ala Lys Lys
        275                 280                 285
Lys Ile Val Glu Ala Ala Lys Ala Asn Glu Gly Leu Gly Leu Gln
    290                 295                 300
Asn Cys Ala Thr His Thr Glu Ile Lys Leu Met Lys Asn Arg Glu Pro
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Leu Asp Met Ala Gln Leu Leu Leu Asp
            340                 345                 350
Val Leu Cys Phe Gly Lys Asp Ala Asp Leu Pro Asp Gly Leu Leu Asp
        355                 360                 365
Gln Glu Pro Tyr Tyr Val Ala Asp Cys His Leu Tyr Pro Gln His Phe
    370                 375                 380
Lys Gln Asn Gly Gln Ile Pro Glu Thr Ala Glu Asp Leu Val Ile Glu
385                 390                 395                 400
Ala Ile Asp Ile Pro Asp Gly Leu Leu Lys Gly Asp Thr Glu Ile Val
                405                 410                 415
Ser Phe Ser Ala Ala Pro Gly Thr Ser Val Asp Leu Thr Leu Phe
            420                 425                 430
Glu Ala Phe Asn Ser Ile Ala Ala Phe Glu Leu Lys Gly Ser Asn Ser
        435                 440                 445
Gln Asp Val Ala Glu Ser Ile Arg Gln Ile Gln Gln His Ala Lys Leu
    450                 455                 460
Thr Ala Lys Tyr Val Leu Pro Val
465                 470

<210> SEQ ID NO 9
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108E/H378K)

<400> SEQUENCE: 9

Met Glu Arg Lys Thr Val Leu Val Ile Ala Asp Leu Gly Gly Cys Pro
1               5                   10                  15
Pro His Met Phe Tyr Lys Ser Ala Ala Glu Lys Tyr Asn Leu Val Ser
            20                  25                  30
Phe Ile Pro Arg Pro Phe Ala Ile Thr Ala Ser His Ala Ala Leu Ile
        35                  40                  45
Glu Lys Tyr Ser Val Ala Val Ile Lys Asp Lys Asp Tyr Phe Lys Ser
    50                  55                  60

```
Leu Ala Asp Phe Glu His Pro Asp Ser Ile Tyr Trp Ala His Glu Asp
 65              70                  75                  80

His Asn Lys Pro Glu Glu Val Val Glu Gln Ile Val Lys Val Ala
             85                  90                  95

Glu Met Phe Gly Ala Asp Ala Ile Thr Thr Asn Glu Glu Leu Phe Ile
            100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
            130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
            165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
            210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
            245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
            290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
            325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys Lys Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
            405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470
```

```
<210> SEQ ID NO 10
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108E/H378R)

<400> SEQUENCE: 10

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Glu Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365
```

```
Gln Glu Pro Tyr Tyr Val Ala Asp Cys Arg Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 11
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108Q/I112V)

<400> SEQUENCE: 11

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Gln Glu Leu Phe Val
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255
```

```
Tyr Phe Pro Ile Ala Ile His Asp Lys Thr Pro Gln Ile Gly Phe Thr
                260                 265                 270

Glu Thr Ser His Ile Thr Pro Ser Ile Leu Asp Glu Ala Lys Lys
            275                 280                 285

Lys Ile Val Glu Ala Ala Lys Lys Ala Asn Glu Gly Leu Gly Leu Gln
        290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 12
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108Q/H378K)

<400> SEQUENCE: 12

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Gln Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
```

```
            130                 135                 140
Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
                180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
            210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
                260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
            290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
                355                 360                 365

Gln Glu Pro Tyr Tyr Val Ala Asp Cys Lys Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470
```

<210> SEQ ID NO 13
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108Q/H378R)

<400> SEQUENCE: 13

```
Met Glu Arg Lys Thr Val Leu Val Ile Ala Asp Leu Gly Gly Cys Pro
1               5                   10                  15
```

-continued

```
Pro His Met Phe Tyr Lys Ser Ala Ala Glu Lys Tyr Asn Leu Val Ser
             20                  25                  30
Phe Ile Pro Arg Pro Phe Ala Ile Thr Ala Ser His Ala Ala Leu Ile
         35                  40                  45
Glu Lys Tyr Ser Val Ala Val Ile Lys Asp Lys Asp Tyr Phe Lys Ser
     50                  55                  60
Leu Ala Asp Phe Glu His Pro Asp Ser Ile Tyr Trp Ala His Glu Asp
 65                  70                  75                  80
His Asn Lys Pro Glu Glu Val Val Glu Gln Ile Val Lys Val Ala
                 85                  90                  95
Glu Met Phe Gly Ala Asp Ala Ile Thr Thr Asn Gln Glu Leu Phe Ile
             100                 105                 110
Ala Pro Met Ala Lys Ala Cys Glu Arg Leu Gly Leu Arg Gly Ala Gly
         115                 120                 125
Val Gln Ala Ala Glu Asn Ala Arg Asp Lys Asn Lys Met Arg Asp Ala
     130                 135                 140
Phe Asn Lys Ala Gly Val Lys Ser Ile Lys Asn Lys Arg Val Thr Thr
145                 150                 155                 160
Leu Glu Asp Phe Arg Ala Ala Leu Glu Glu Ile Gly Thr Pro Leu Ile
             165                 170                 175
Leu Lys Pro Thr Tyr Leu Ala Ser Ser Ile Gly Val Thr Leu Ile Thr
         180                 185                 190
Asp Thr Glu Thr Ala Glu Asp Glu Phe Asn Arg Val Asn Asp Tyr Leu
     195                 200                 205
Lys Ser Ile Asn Val Pro Lys Ala Val Thr Phe Glu Ala Pro Phe Ile
210                 215                 220
Ala Glu Glu Phe Leu Gln Gly Glu Tyr Gly Asp Trp Tyr Gln Thr Glu
225                 230                 235                 240
Gly Tyr Ser Asp Tyr Ile Ser Ile Glu Gly Ile Met Ala Asp Gly Glu
             245                 250                 255
Tyr Phe Pro Ile Ala Ile His Asp Lys Thr Pro Gln Ile Gly Phe Thr
         260                 265                 270
Glu Thr Ser His Ile Thr Pro Ser Ile Leu Asp Glu Glu Ala Lys Lys
     275                 280                 285
Lys Ile Val Glu Ala Ala Lys Lys Ala Asn Glu Gly Leu Gly Leu Gln
290                 295                 300
Asn Cys Ala Thr His Thr Glu Ile Lys Leu Met Lys Asn Arg Glu Pro
305                 310                 315                 320
Gly Leu Ile Glu Ser Ala Ala Arg Phe Ala Gly Trp Asn Met Ile Pro
             325                 330                 335
Asn Ile Lys Lys Val Phe Gly Leu Asp Met Ala Gln Leu Leu Leu Asp
         340                 345                 350
Val Leu Cys Phe Gly Lys Asp Ala Asp Leu Pro Asp Gly Leu Leu Asp
     355                 360                 365
Gln Glu Pro Tyr Tyr Val Ala Asp Cys Arg Leu Tyr Pro Gln His Phe
370                 375                 380
Lys Gln Asn Gly Gln Ile Pro Glu Thr Ala Glu Asp Leu Val Ile Glu
385                 390                 395                 400
Ala Ile Asp Ile Pro Asp Gly Leu Leu Lys Gly Asp Thr Glu Ile Val
             405                 410                 415
Ser Phe Ser Ala Ala Pro Gly Thr Ser Val Asp Leu Thr Leu Phe
         420                 425                 430
Glu Ala Phe Asn Ser Ile Ala Ala Phe Glu Leu Lys Gly Ser Asn Ser
```

<210> SEQ ID NO 14
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108A/I112V/H378R)

<400> SEQUENCE: 14

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Ala Glu Leu Phe Val
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

-continued

```
Gly Leu Ile Glu Ser Ala Ala Arg Phe Ala Gly Trp Asn Met Ile Pro
            325                 330                 335

Asn Ile Lys Lys Val Phe Gly Leu Asp Met Ala Gln Leu Leu Leu Asp
        340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys Arg Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470
```

<210> SEQ ID NO 15
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108Q/I112V/H378K)

<400> SEQUENCE: 15

```
Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Gln Glu Leu Phe Val
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205
```

```
Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys Lys Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 16
<211> LENGTH: 472
<212> TYPE: PRT
<213> ORGANISM: Bacillus subtilis
<220> FEATURE:
<221> NAME/KEY: MISC_FEATURE
<223> OTHER INFORMATION: YwfE (mutant type: N108Q/I112V/H378R)

<400> SEQUENCE: 16

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
```

```
                    85                  90                  95
Glu Met Phe Gly Ala Asp Ala Ile Thr Thr Asn Gln Glu Leu Phe Val
                100                 105                 110
Ala Pro Met Ala Lys Ala Cys Glu Arg Leu Gly Leu Arg Gly Ala Gly
                115                 120                 125
Val Gln Ala Ala Glu Asn Ala Arg Asp Lys Asn Lys Met Arg Asp Ala
                130                 135                 140
Phe Asn Lys Ala Gly Val Lys Ser Ile Lys Asn Lys Arg Val Thr Thr
145                 150                 155                 160
Leu Glu Asp Phe Arg Ala Ala Leu Glu Glu Ile Gly Thr Pro Leu Ile
                165                 170                 175
Leu Lys Pro Thr Tyr Leu Ala Ser Ser Ile Gly Val Thr Leu Ile Thr
                180                 185                 190
Asp Thr Glu Thr Ala Glu Asp Glu Phe Asn Arg Val Asn Asp Tyr Leu
                195                 200                 205
Lys Ser Ile Asn Val Pro Lys Ala Val Thr Phe Glu Ala Pro Phe Ile
                210                 215                 220
Ala Glu Glu Phe Leu Gln Gly Glu Tyr Gly Asp Trp Tyr Gln Thr Glu
225                 230                 235                 240
Gly Tyr Ser Asp Tyr Ile Ser Ile Glu Gly Ile Met Ala Asp Gly Glu
                245                 250                 255
Tyr Phe Pro Ile Ala Ile His Asp Lys Thr Pro Gln Ile Gly Phe Thr
                260                 265                 270
Glu Thr Ser His Ile Thr Pro Ser Ile Leu Asp Glu Ala Lys Lys
                275                 280                 285
Lys Ile Val Glu Ala Lys Lys Ala Asn Glu Gly Leu Gly Leu Gln
                290                 295                 300
Asn Cys Ala Thr His Thr Glu Ile Lys Leu Met Lys Asn Arg Glu Pro
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Leu Asp Met Ala Gln Leu Leu Leu Asp
                340                 345                 350
Val Leu Cys Phe Gly Lys Asp Ala Asp Leu Pro Asp Gly Leu Leu Asp
                355                 360                 365
Gln Glu Pro Tyr Tyr Val Ala Asp Cys Arg Leu Tyr Pro Gln His Phe
                370                 375                 380
Lys Gln Asn Gly Gln Ile Pro Glu Thr Ala Glu Asp Leu Val Ile Glu
385                 390                 395                 400
Ala Ile Asp Ile Pro Asp Gly Leu Leu Lys Gly Asp Thr Glu Ile Val
                405                 410                 415
Ser Phe Ser Ala Ala Pro Gly Thr Ser Val Asp Leu Thr Leu Phe
                420                 425                 430
Glu Ala Phe Asn Ser Ile Ala Ala Phe Glu Leu Lys Gly Ser Asn Ser
                435                 440                 445
Gln Asp Val Ala Glu Ser Ile Arg Gln Ile Gln Gln His Ala Lys Leu
                450                 455                 460
Thr Ala Lys Tyr Val Leu Pro Val
465                 470

<210> SEQ ID NO 17
<211> LENGTH: 1419
<212> TYPE: DNA
<213> ORGANISM: Bacillus subtilis
```

```
<220> FEATURE:
<221> NAME/KEY: misc_feature
<223> OTHER INFORMATION: YwfE (wild type)

<400> SEQUENCE: 17
atggagagaa aaacagtatt ggtcatcgct gatcttggag gctgcccgcc gcacatgttt        60
tataaaagcg ctgctgaaaa atataacctg gtcagcttta ttccaagacc ttttgcaatt       120
acagcctccc atgcagcatt gattgaaaaa tactcggtcg cggtcataaa agataaagac       180
tattttaaga gtttagctga ttttgaacac cctgattcca tttattgggc gcatgaagat       240
cataacaagc tgaggaaga ggtcgtcgag caaatcgtca aggttgccga atgtttggg         300 gcggatgcca tcacaacaaa caatgaatta ttcattgctc cgatggcgaa agcctgtgaa       360
cgtctgggct tgagaggtgc cggcgtgcag gcagccgaaa atgccagaga taaaaataaa       420
atgagggacg cttttaataa ggccggagtc aaatcgatca aaaacaaacg agtcacaact       480
cttgaagatt ccgtgctgc tcttgaagag atcggcacac ctcttatctt aaagcctaca       540
tacttagcga gttctatcgg tgtaacgctg attacgaca ctgagacggc agaagatgaa       600
tttaacagag tcaatgacta tctgaaatca attaacgtgc caaaggcggt tacgtttgaa       660
gcgccgttta tcgctgaaga atttttacag ggtgagtacg gagactggta tcaaacagaa       720
gggtactccg actatatcag tatagaaggc atcatggctg acggtgagta tttcccgatc       780
gccattcatg ataaaacgcc gcaaatcggg tttacagaga catcccacat tacgccgtcc       840
attctggatg aagaggcaaa aaagaaaatt gtcgaagctg ccaaaaaggc aaatgaaggg       900
cttggactgc aaaattgcgc aacacataca gagatcaagc taatgaaaaa cagagaaccg       960
ggtttaatag agtcggcagc cagatttgcc ggctggaata tgatccccaa tattaaaaag      1020
gtctttggcc ttgatatggc gcaattatta ttagatgtcc tctgtttcgg aaaagacgcc      1080
gatctgccgg acgattatt ggatcaagag ccttattatg ttgccgactg ccatttgtac       1140
ccgcagcatt tcaaacaaaa tggccaaatt cctgaaactg ctgaggattt ggtcattgaa      1200
gcgatcgata ttccggacgg gcttttaaaa ggggatactg aaatcgtttc tttttcggcc      1260
gcagcaccag gcacttcagt tgatttgaca ttgtttgaag cttcaattc cattgctgca       1320 tttgaactga aaggcagtaa ttcacaggat gtggctgaat caatcagaca aattcagcag      1380
catgcgaagc tgacggcaaa gtatgtgctg ccagtatga                              1419

<210> SEQ ID NO 18
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108A)

<400> SEQUENCE: 18
atggagagaa aaacagtatt ggtcatcgct gatcttggag gctgcccgcc gcacatgttt        60
tataaaagcg ctgctgaaaa atataacctg gtcagcttta ttccaagacc ttttgcaatt       120
acagcctccc atgcagcatt gattgaaaaa tactcggtcg cggtcataaa agataaagac       180
tattttaaga gtttagctga ttttgaacac cctgattcca tttattgggc gcatgaagat       240
cataacaagc tgaggaaga ggtcgtcgag caaatcgtca aggttgccga atgtttggg         300 gcggatgcca tcacaacaaa cgcggaatta ttcattgctc cgatggcgaa agcctgtgaa       360
cgtctgggct tgagaggtgc cggcgtgcag gcagccgaaa atgccagaga taaaaataaa       420
```

```
atgagggacg cttttaataa ggccggagtc aaatcgatca aaaacaaacg agtcacaact      480
cttgaagatt tccgtgctgc tcttgaagag atcggcacac ctcttatctt aaagcctaca      540
tacttagcga gttctatcgg tgtaacgctg attacggaca ctgagacggc agaagatgaa      600
tttaacagag tcaatgacta tctgaaatca attaacgtgc caaggcggt tacgtttgaa       660 gcgccgttta tcgctgaaga atttttacag ggtgagtacg gagactggta tcaaacagaa      720
gggtactccg actatatcag tatagaaggc atcatggctg acggtgagta tttcccgatc      780
gccattcatg ataaaacgcc gcaaatcggg tttacagaga catcccacat tacgccgtcc      840
attctggatg aagaggcaaa aaagaaaatt gtcgaagctg ccaaaaaggc aaatgaaggg      900
cttggactgc aaaattgcgc aacacataca gagatcaagc taatgaaaaa cagagaaccg      960
ggtttaatag agtcggcagc cagatttgcc ggctggaata tgatccccaa tattaaaaag     1020
gtctttggcc ttgatatggc gcaattatta ttagatgtcc tctgtttcgg aaaagacgcc     1080
gatctgccgg acggattatt ggatcaagag ccttattatg ttgccgactg ccatttgtac     1140
ccgcagcatt tcaaacaaaa tggccaaatt cctgaaactc tgaggatttt ggtcattgaa     1200
gcgatcgata ttccggacgg gcttttaaaa ggggatactg aaatcgtttc ttttcggcc      1260 gcagcaccag gcacttcagt tgatttgaca ttgtttgaag ctttcaattc cattgctgca     1320
tttgaactga aaggcagtaa ttcacaggat gtggctgaat caatcagaca aattcagcag     1380
catgcgaagc tgacggcaaa gtatgtgctg ccagtatga                            1419
```

<210> SEQ ID NO 19
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108E)

<400> SEQUENCE: 19

```
atggagagaa aaacagtatt ggtcatcgct gatcttggag gctgcccgcc gcacatgttt       60
tataaaagcg ctgctgaaaa atataacctg gtcagcttta ttccaagacc ttttgcaatt      120
acagcctccc atgcagcatt gattgaaaaa tactcggtcg cggtcataaa agataaagac      180
tattttaaga gtttagctga ttttgaacac cctgattcca tttattgggc gcatgaagat      240
cataacaagc ctgaggaaga ggtcgtcgag caaatcgtca aggttgccga atgtttggg       300 gcggatgcca tcacaacaaa cgaagaatta ttcattgctc cgatggcgaa agcctgtgaa      360
cgtctgggct tgagaggtgc cggcgtgcag gcagccgaaa tgccagaga taaaaataaa       420 atgagggacg cttttaataa ggccggagtc aaatcgatca aaaacaaacg agtcacaact      480
cttgaagatt tccgtgctgc tcttgaagag atcggcacac ctcttatctt aaagcctaca      540
tacttagcga gttctatcgg tgtaacgctg attacggaca ctgagacggc agaagatgaa      600
tttaacagag tcaatgacta tctgaaatca attaacgtgc caaggcggt tacgtttgaa       660 gcgccgttta tcgctgaaga atttttacag ggtgagtacg gagactggta tcaaacagaa      720
gggtactccg actatatcag tatagaaggc atcatggctg acggtgagta tttcccgatc      780
gccattcatg ataaaacgcc gcaaatcggg tttacagaga catcccacat tacgccgtcc      840
attctggatg aagaggcaaa aaagaaaatt gtcgaagctg ccaaaaaggc aaatgaaggg      900
cttggactgc aaaattgcgc aacacataca gagatcaagc taatgaaaaa cagagaaccg      960
ggtttaatag agtcggcagc cagatttgcc ggctggaata tgatccccaa tattaaaaag     1020
```

```
gtctttggcc ttgatatggc gcaattatta ttagatgtcc tctgtttcgg aaaagacgcc    1080
gatctgccgg acggattatt ggatcaagag ccttattatg ttgccgactg ccatttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc     1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                           1419

<210> SEQ ID NO 20
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108Q)

<400> SEQUENCE: 20
atggagagaa aaacagtatt ggtcatcgct gatcttggag gctgcccgcc gcacatgttt    60
tataaaagcg ctgctgaaaa atataacctg gtcagcttta ttccaagacc ttttgcaatt    120
acagcctccc atgcagcatt gattgaaaaa tactcggtcg cggtcataaa agataaagac    180
tattttaaga gttagctga ttttgaacac cctgattcca tttattgggc gcatgaagat    240
cataacaagc ctgaggaaga ggtcgtcgag caaatcgtca aggttgccga atgtttggg     300 gcggatgcca tcacaacaaa ccaggaatta ttcattgctc cgatggcgaa agcctgtgaa    360
cgtctgggct tgagaggtgc cggcgtgcag gcagccgaaa atgccagaga taaaaataaa    420
atgagggacg cttttaataa ggccggagtc aaatcgatca aaaacaaacg agtcacaact    480
cttgaagatt tccgtgctgc tcttgaagag atcggcacac ctcttatctt aaagcctaca    540
tacttagcga gttctatcgg tgtaacgctg attacggaca ctgagacggc agaagatgaa    600
tttaacagag tcaatgacta tctgaaatca attaacgtgc caaggcggt tacgtttgaa    660 gcgccgttta tcgctgaaga ttttttacag ggtgagtacg gagactggta tcaaacagaa    720
gggtactccg actatatcag tatagaaggc atcatggctg acggtgagta tttcccgatc    780
gccattcatg ataaaacgcc gcaaatcggg tttacagaga catcccacat tacgccgtcc    840
attctggatg aagaggcaaa aaagaaaatt gtcgaagctc caaaaaggc aaatgaaggg    900 cttggactgc aaaattgcgc aacacataca gagatcaagc taatgaaaaa cagagaaccg    960
ggtttaatag agtcggcagc cagatttgcc ggctggaata tgatccccaa tattaaaaag    1020
gtctttggcc ttgatatggc gcaattatta ttagatgtcc tctgtttcgg aaaagacgcc    1080
gatctgccgg acggattatt ggatcaagag ccttattatg ttgccgactg ccatttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc     1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                           1419

<210> SEQ ID NO 21
<211> LENGTH: 1419
<212> TYPE: DNA
<213> ORGANISM: Bacillus subtilis
<220> FEATURE:
```

<221> NAME/KEY: misc_feature
<223> OTHER INFORMATION: YwfE (mutant type: N108A/I112V)

<400> SEQUENCE: 21

| | |
|---|---|
| atggagagaa aaacagtatt ggtcatcgct gatcttggag gctgcccgcc gcacatgttt | 60 |
| tataaaagcg ctgctgaaaa atataacctg gtcagcttta ttccaagacc ttttgcaatt | 120 |
| acagcctccc atgcagcatt gattgaaaaa tactcggtcg cggtcataaa agataaagac | 180 |
| tattttaaga gtttagctga ttttgaacac cctgattcca tttattgggc gcatgaagat | 240 |
| cataacaagc ctgaggaaga ggtcgtcgag caaatcgtca aggttgccga atgtttggg | 300 |
| gcggatgcca tcacaacaaa cgcggaatta ttcgtggctc cgatggcgaa agcctgtgaa | 360 |
| cgtctgggct tgagaggtgc cggcgtgcag gcagccgaaa atgccagaga taaaaataaa | 420 |
| atgagggacg cttttaataa ggccggagtc aaatcgatca aaaacaaacg agtcacaact | 480 |
| cttgaagatt ccgtgctgc tcttgaagag atcggcacac ctcttatctt aaagcctaca | 540 |
| tacttagcga gttctatcgg tgtaacgctg attacggaca ctgagacggc agaagatgaa | 600 |
| tttaacagag tcaatgacta tctgaaatca attaacgtgc caaaggcggt tacgtttgaa | 660 |
| gcgccgttta tcgctgaaga atttttacag ggtgagtacg gagactggta tcaaacagaa | 720 |
| gggtactccg actatatcag tatagaaggc atcatggctg acggtgagta tttcccgatc | 780 |
| gccattcatg ataaaacgcc gcaaatcggg tttacagaga catcccacat tacgccgtcc | 840 |
| attctggatg aagaggcaaa aaagaaaatt gtcgaagctg ccaaaaaggc aaatgaaggg | 900 |
| cttggactgc aaaattgcgc aacacataca gagatcaagc taatgaaaaa cagagaaccg | 960 |
| ggtttaatag agtcggcagc cagatttgcc ggctggaata tgatccccaa tattaaaaag | 1020 |
| gtctttggcc ttgatatggc gcaattatta ttagatgtcc tctgtttcgg aaaagacgcc | 1080 |
| gatctgccgg acggattatt ggatcaagag cctattatg ttgccgactg ccatttgtac | 1140 |
| ccgcagcatt tcaaacaaaa tggccaaatt cctgaaactg ctgaggattt ggtcattgaa | 1200 |
| gcgatcgata ttccggacgg gcttttaaaa ggggatactg aaatcgtttc ttttcggcc | 1260 |
| gcagcaccag gcacttcagt tgatttgaca ttgtttgaag cttttcaattc cattgctgca | 1320 |
| tttgaactga aaggcagtaa ttcacaggat gtggctgaat caatcagaca aattcagcag | 1380 |
| catgcgaagc tgacggcaaa gtatgtgctg ccagtatga | 1419 |

<210> SEQ ID NO 22
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108A/H378K)

<400> SEQUENCE: 22

| | |
|---|---|
| atggagagaa aaacagtatt ggtcatcgct gatcttggag gctgcccgcc gcacatgttt | 60 |
| tataaaagcg ctgctgaaaa atataacctg gtcagcttta ttccaagacc ttttgcaatt | 120 |
| acagcctccc atgcagcatt gattgaaaaa tactcggtcg cggtcataaa agataaagac | 180 |
| tattttaaga gtttagctga ttttgaacac cctgattcca tttattgggc gcatgaagat | 240 |
| cataacaagc ctgaggaaga ggtcgtcgag caaatcgtca aggttgccga atgtttggg | 300 |
| gcggatgcca tcacaacaaa cgcggaatta ttcattgctc cgatggcgaa agcctgtgaa | 360 |
| cgtctgggct tgagaggtgc cggcgtgcag gcagccgaaa atgccagaga taaaaataaa | 420 |
| atgagggacg cttttaataa ggccggagtc aaatcgatca aaaacaaacg agtcacaact | 480 |

```
cttgaagatt tccgtgctgc tcttgaagag atcggcacac ctcttatctt aaagcctaca        540
tacttagcga gttctatcgg tgtaacgctg attacggaca ctgagacggc agaagatgaa        600
tttaacagag tcaatgacta tctgaaatca attaacgtgc caaaggcggt tacgtttgaa        660
gcgccgttta tcgctgaaga attttttacag ggtgagtacg gagactggta tcaaacagaa       720
gggtactccg actatatcag tatagaaggc atcatggctg acggtgagta tttcccgatc        780
gccattcatg ataaaacgcc gcaaatcggg tttacagaga catcccacat tacgccgtcc        840
attctggatg aagaggcaaa aaagaaaatt gtcgaagctg ccaaaaaggc aaatgaaggg        900
cttggactgc aaaattgcgc aacacataca gagatcaagc taatgaaaaa cagagaaccg        960
ggtttaatag agtcggcagc cagatttgcc ggctggaata tgatccccaa tattaaaaag       1020
gtctttggcc ttgatatggc gcaattatta ttagatgtcc tctgtttcgg aaaagacgcc       1080
gatctgccgg acggattatt ggatcaagag ccttattatg ttgccgactg caaattgtac       1140
ccgcagcatt tcaaacaaaa tggccaaatt cctgaaactg ctgaggattt ggtcattgaa       1200
gcgatcgata ttccggacgg gcttttaaaa ggggatactg aaatcgtttc ttttcggcc       1260 gcagcaccag gcacttcagt tgatttgaca ttgtttgaag cttcaattc cattgctgca       1320 tttgaactga aaggcagtaa ttcacaggat gtggctgaat caatcagaca aattcagcag       1380
catgcgaagc tgacggcaaa gtatgtgctg ccagtatga                             1419

<210> SEQ ID NO 23
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108A/H378R)

<400> SEQUENCE: 23
atggagagaa aaacagtatt ggtcatcgct gatcttggag ctgcccgcc gcacatgttt        60 tataaaagcg ctgctgaaaa atataacctg gtcagcttta ttccaagacc ttttgcaatt       120
acagcctccc atgcagcatt gattgaaaaa tactcggtcg cggtcataaa agataaagac       180
tattttaaga gtttagctga ttttgaacac cctgattcca tttattgggc gcatgaagat       240
cataacaagc ctgaggaaga ggtcgtcgag caaatcgtca aggttgccga atgtttggg        300 gcggatgcca tcacaacaaa cgcggaatta ttcattgctc cgatggcgaa agcctgtgaa       360
cgtctgggct tgagaggtgc cggcgtgcag gcagccgaaa atgccagaga taaaaataaa       420
atgagggacg cttttaataa ggccggagtc aaatcgatca aaaacaaacg agtcacaact       480
cttgaagatt ccgtgctgc tcttgaagag atcggcacac ctcttatctt aaagcctaca        540
tacttagcga gttctatcgg tgtaacgctg attacggaca ctgagacggc agaagatgaa        600
tttaacagag tcaatgacta tctgaaatca attaacgtgc caaaggcggt tacgtttgaa        660
gcgccgttta tcgctgaaga attttttacag ggtgagtacg gagactggta tcaaacagaa       720
gggtactccg actatatcag tatagaaggc atcatggctg acggtgagta tttcccgatc        780
gccattcatg ataaaacgcc gcaaatcggg tttacagaga catcccacat tacgccgtcc        840
attctggatg aagaggcaaa aaagaaaatt gtcgaagctg ccaaaaaggc aaatgaaggg        900
cttggactgc aaaattgcgc aacacataca gagatcaagc taatgaaaaa cagagaaccg        960
ggtttaatag agtcggcagc cagatttgcc ggctggaata tgatccccaa tattaaaaag       1020
gtctttggcc ttgatatggc gcaattatta ttagatgtcc tctgtttcgg aaaagacgcc       1080
```

```
gatctgccgg acggattatt ggatcaagag ccttattatg ttgccgactg ccgcttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc     1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                          1419
```

<210> SEQ ID NO 24
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108E/I112V)

<400> SEQUENCE: 24

```
atggagagaa aaacagtatt ggtcatcgct gatcttggag gctgcccgcc gcacatgttt     60
tataaaagcg ctgctgaaaa atataacctg gtcagcttta ttccaagacc ttttgcaatt    120
acagcctccc atgcagcatt gattgaaaaa tactcggtcg cggtcataaa agataaagac    180
tattttaaga gtttagctga ttttgaacac cctgattcca tttattgggc gcatgaagat    240
cataacaagc tgaggaaga ggtcgtcgag caaatcgtca aggttgccga aatgtttggg     300
gcggatgcca tcacaacaaa cgaagaatta ttcgtggctc cgatggcgaa agcctgtgaa    360
cgtctgggct tgagaggtgc cggcgtgcag gcagccgaaa atgccagaga taaaaataaa    420
atgagggacg ctttttaataa ggccggagtc aaatcgatca aaaacaaacg agtcacaact   480
cttgaagatt tccgtgctgc tcttgaagag atcggcacac ctcttatctt aaagcctaca    540
tacttagcga gttctatcgg tgtaacgctg attacggaca ctgagacggc agaagatgaa    600
tttaacagag tcaatgacta tctgaaatca attaacgtgc caaaggcggt tacgtttgaa    660
gcgccgttta tcgctgaaga attttttacag ggtgagtacg gagactggta tcaaacagaa   720
gggtactccg actatatcag tatagaaggc atcatggctg acggtgagta tttcccgatc    780
gccattcatg ataaaacgcc gcaaatcggg tttacagaga catcccacat tacgccgtcc    840
attctggatg aagaggcaaa aaagaaaatt gtcgaagctg ccaaaaaggc aaatgaaggg    900
cttggactgc aaaattgcgc aacacataca gagatcaagc taatgaaaaa cagagaaccg    960
ggtttaatag agtcggcagc cagatttgcc ggctggaata tgatccccaa tattaaaaag   1020
gtctttggcc ttgatatggc gcaattatta ttagatgtcc tctgtttcgg aaaagacgcc   1080
gatctgccgg acggattatt ggatcaagag ccttattatg ttgccgactg ccatttgtac   1140
ccgcagcatt tcaaacaaaa tggccaaatt cctgaaactg ctgaggattt ggtcattgaa   1200
gcgatcgata ttccggacgg gcttttaaaa ggggatactg aaatcgtttc ttttcggcc    1260 gcagcaccag gcacttcagt tgatttgaca ttgtttgaag ctttcaattc cattgctgca   1320
tttgaactga aaggcagtaa ttcacaggat gtggctgaat caatcagaca aattcagcag   1380
catgcgaagc tgacggcaaa gtatgtgctg ccagtatga                          1419
```

<210> SEQ ID NO 25
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108E/H378K)

<400> SEQUENCE: 25

```
atggagagaa aaacagtatt ggtcatcgct gatcttggag gctgcccgcc gcacatgttt      60
tataaaagcg ctgctgaaaa atataacctg gtcagcttta ttccaagacc ttttgcaatt     120
acagcctccc atgcagcatt gattgaaaaa tactcggtcg cggtcataaa agataaagac     180
tattttaaga gttagctga ttttgaacac cctgattcca tttattgggc gcatgaagat      240
cataacaagc ctgaggaaga ggtcgtcgag caaatcgtca aggttgccga atgtttggg      300
gcggatgcca tcacaacaaa cgaagaatta ttcattgctc cgatggcgaa agcctgtgaa     360
cgtctgggct tgagaggtgc cggcgtgcag gcagccgaaa atgccagaga taaaaataaa     420
atgagggacg cttttaataa ggccggagtc aaatcgatca aaaacaaacg agtcacaact     480
cttgaagatt ccgtgctgc tcttgaagag atcggcacac ctcttatctt aaagcctaca      540
tacttagcga gttctatcgg tgtaacgctg attacggaca ctgagacggc agaagatgaa     600
tttaacagag tcaatgacta tctgaaatca attaacgtgc caaggcggt tacgtttgaa      660
gcgccgttta tcgctgaaga ttttttacag ggtgagtacg gagactggta tcaaacagaa     720
gggtactccg actatatcag tatagaaggc atcatggctg acggtgagta tttcccgatc     780
gccattcatg ataaaacgcc gcaaatcggg tttacagaga catcccacat tacgccgtcc     840
attctggatg aagaggcaaa aaagaaaatt gtcgaagctg ccaaaaaggc aaatgaaggg     900
cttggactgc aaaattgcgc aacacataca gagatcaagc taatgaaaaa cagagaaccg     960
ggtttaatag agtcggcagc cagatttgcc ggctggaata tgatccccaa tattaaaaag    1020
gtctttggcc ttgatatggc gcaattatta ttagatgtcc tctgtttcgg aaaagacgcc    1080
gatctgccgg acggattatt ggatcaagag cctattatg ttgccgactg caaattgtac     1140
ccgcagcatt tcaaacaaaa tggccaaatt cctgaaactg ctgaggattt ggtcattgaa    1200
gcgatcgata ttccggacgg gcttttaaaa ggggatactg aaatcgtttc tttttcggcc    1260
gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                            1419
```

<210> SEQ ID NO 26
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108E/H378R)

<400> SEQUENCE: 26

```
atggagagaa aaacagtatt ggtcatcgct gatcttggag gctgcccgcc gcacatgttt      60
tataaaagcg ctgctgaaaa atataacctg gtcagcttta ttccaagacc ttttgcaatt     120
acagcctccc atgcagcatt gattgaaaaa tactcggtcg cggtcataaa agataaagac     180
tattttaaga gttagctga ttttgaacac cctgattcca tttattgggc gcatgaagat      240
cataacaagc ctgaggaaga ggtcgtcgag caaatcgtca aggttgccga atgtttggg      300
gcggatgcca tcacaacaaa cgaagaatta ttcattgctc cgatggcgaa agcctgtgaa     360
cgtctgggct tgagaggtgc cggcgtgcag gcagccgaaa atgccagaga taaaaataaa     420
atgagggacg cttttaataa ggccggagtc aaatcgatca aaaacaaacg agtcacaact     480
```

-continued

```
cttgaagatt tccgtgctgc tcttgaagag atcggcacac ctcttatctt aaagcctaca    540
tacttagcga gttctatcgg tgtaacgctg attacggaca ctgagacggc agaagatgaa    600
tttaacagag tcaatgacta tctgaaatca attaacgtgc aaaggcggt tacgtttgaa     660
gcgccgttta tcgctgaaga attttttacag ggtgagtacg gagactggta tcaaacagaa   720
gggtactccg actatatcag tatagaaggc atcatggctg acggtgagta tttcccgatc    780
gccattcatg ataaaacgcc gcaaatcggg tttacagaga catcccacat tacgccgtcc    840
attctggatg aagaggcaaa aagaaaatt gtcgaagctg ccaaaaaggc aaatgaaggg     900
cttggactgc aaaattgcgc aacacataca gagatcaagc taatgaaaaa cagagaaccg    960
ggtttaatag agtcggcagc cagatttgcc ggctggaata tgatccccaa tattaaaaag   1020
gtctttggcc ttgatatggc gcaattatta ttagatgtcc tctgtttcgg aaaagacgcc   1080
gatctgccgg acggattatt ggatcaagag ccttattatg ttgccgactg ccgcttgtac   1140
ccgcagcatt tcaaacaaaa tggccaaatt cctgaaactg ctgaggattt ggtcattgaa   1200
gcgatcgata ttccggacgg gctttttaaa ggggatactg aaatcgtttc ttttttcggcc  1260
gcagcaccag gcacttcagt tgatttgaca ttgtttgaag cttttcaattc cattgctgca  1320
tttgaactga aaggcagtaa ttcacaggat gtggctgaat caatcagaca aattcagcag   1380
catgcgaagc tgacggcaaa gtatgtgctg ccagtatga                         1419
```

<210> SEQ ID NO 27
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108Q/I112V)

<400> SEQUENCE: 27

```
atggagagaa aaacagtatt ggtcatcgct gatcttggag ctgcccgcc gcacatgttt     60
tataaaagcg ctgctgaaaa atataacctg gtcagcttta ttccaagacc ttttgcaatt   120
acagcctccc atgcagcatt gattgaaaaa tactcggtcg cggtcataaa agataaagac   180
tattttaaga gtttagctga ttttgaacac cctgattcca tttattgggc gcatgaagat   240
cataacaagc tgaggaaga ggtcgtcgag caaatcgtca aggttgccga atgtttggg     300
gcggatgcca tcacaacaaa ccaggaatta ttcgtggctc cgatggcgaa agcctgtgaa   360
cgtctgggct tgagaggtgc cggcgtgcag gcagccgaaa atgccagaga taaaaataaa   420
atgagggacg cttttaataa ggccggagtc aaatcgatca aaaacaaacg agtcacaact   480
cttgaagatt ccgtgctgc tcttgaagag atcggcacac ctcttatctt aaagcctaca    540
tacttagcga gttctatcgg tgtaacgctg attacggaca ctgagacggc agaagatgaa   600
tttaacagag tcaatgacta tctgaaatca attaacgtgc aaaggcggt tacgtttgaa    660
gcgccgttta tcgctgaaga attttttacag ggtgagtacg gagactggta tcaaacagaa  720
gggtactccg actatatcag tatagaaggc atcatggctg acggtgagta tttcccgatc   780
gccattcatg ataaaacgcc gcaaatcggg tttacagaga catcccacat tacgccgtcc   840
attctggatg aagaggcaaa aagaaaatt gtcgaagctg ccaaaaaggc aaatgaaggg    900
cttggactgc aaaattgcgc aacacataca gagatcaagc taatgaaaaa cagagaaccg   960
ggtttaatag agtcggcagc cagatttgcc ggctggaata tgatccccaa tattaaaaag  1020
gtctttggcc ttgatatggc gcaattatta ttagatgtcc tctgtttcgg aaaagacgcc  1080
```

```
gatctgccgg acggattatt ggatcaagag ccttattatg ttgccgactg ccatttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc    1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                          1419
```

<210> SEQ ID NO 28
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108Q/H378K)

<400> SEQUENCE: 28

```
atggagagaa aaacagtatt ggtcatcgct gatcttggag ctgcccgcc gcacatgttt      60 tataaaagcg ctgctgaaaa atataacctg gtcagcttta ttccaagacc ttttgcaatt    120
acagcctccc atgcagcatt gattgaaaaa tactcggtcg cggtcataaa agataaagac    180
tattttaaga gtttagctga ttttgaacac cctgattcca tttattgggc gcatgaagat    240
cataacaagc tgaggaaga ggtcgtcgag caaatcgtca aggttgccga atgtttggg     300 gcggatgcca tcacaacaaa ccaggaatta ttcattgctc cgatggcgaa agcctgtgaa    360
cgtctgggct tgagaggtgc cggcgtgcag gcagccgaaa atgccagaga taaaaataaa    420
atgagggacg ctttaataa ggccggagtc aaatcgatca aaaacaaacg agtcacaact    480
cttgaagatt ccgtgctgc tcttgaagag atcggcacac ctcttatctt aaagcctaca    540
tacttagcga gttctatcgg tgtaacgctg attacggaca ctgagacggc agaagatgaa    600
tttaacagag tcaatgacta tctgaaatca attaacgtgc caaaggcggt tacgtttgaa    660
gcgccgttta tcgctgaaga attttttacag ggtgagtacg gagactggta tcaaacagaa    720
gggtactccg actatatcag tatagaaggc atcatggctg acggtgagta tttcccgatc    780
gccattcatg ataaaacgcc gcaaatcggg tttacagaga catcccacat tacgccgtcc    840
attctggatg aagaggcaaa aaagaaaatt gtcgaagctg ccaaaaaggc aaatgaaggg    900
cttggactgc aaaattgcgc aacacataca gagatcaagc taatgaaaaa cagagaaccg    960
ggtttaatag agtcggcagc cagatttgcc ggctggaata tgatcccaa tattaaaaag    1020 gtctttggcc ttgatatggc gcaattatta ttagatgtcc tctgtttcgg aaaagacgcc    1080
gatctgccgg acggattatt ggatcaagag ccttattatg ttgccgactg caaattgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc    1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                          1419
```

<210> SEQ ID NO 29
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108Q/H378R)

<400> SEQUENCE: 29

```
atggagagaa aaacagtatt ggtcatcgct gatcttggag gctgcccgcc gcacatgttt      60
tataaaagcg ctgctgaaaa atataacctg gtcagcttta ttccaagacc ttttgcaatt     120
acagcctccc atgcagcatt gattgaaaaa tactcggtcg cggtcataaa agataaagac     180
tattttaaga gtttagctga ttttgaacac cctgattcca tttattgggc gcatgaagat     240
cataacaagc tgaggaaga ggtcgtcgag caaatcgtca aggttgccga aatgtttggg     300
gcggatgcca tcacaacaaa ccaggaatta ttcattgctc cgatggcgaa agcctgtgaa     360
cgtctgggct tgagaggtgc cggcgtgcag gcagccgaaa atgccagaga taaaaataaa     420
atgagggacg cttttaataa ggccggagtc aaatcgatca aaaacaaacg agtcacaact     480
cttgaagatt tccgtgctgc tcttgaagag atcggcacac ctcttatctt aaagcctaca     540
tacttagcga gttctatcgg tgtaacgctg attacggaca ctgagacggc agaagatgaa     600
tttaacagag tcaatgacta tctgaaatca attaacgtgc caaaggcggt tacgtttgaa     660
gcgccgttta tcgctgaaga atttttacag ggtgagtacg gagactggta tcaaacagaa     720
gggtactccg actatatcag tatagaaggc atcatggctg acggtgagta tttcccgatc     780
gccattcatg ataaaacgcc gcaaatcggg tttacagaga catcccacat tacgccgtcc     840
attctggatg aagaggcaaa aaagaaaatt gtcgaagctg ccaaaaaggc aaatgaaggg     900
cttggactgc aaaattgcgc aacacataca gagatcaagc taatgaaaaa cagagaaccg     960
ggtttaatag agtcggcagc cagatttgcc ggctggaata tgatccccaa tattaaaaag    1020
gtctttggcc ttgatatggc gcaattatta ttagatgtcc tctgtttcgg aaaagacgcc    1080
gatctgccgg acggattatt ggatcaagag cctattatg ttgccgactg ccgcttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc    1260
gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                          1419
```

<210> SEQ ID NO 30
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108A/I112V/H378R)

<400> SEQUENCE: 30

```
atggagagaa aaacagtatt ggtcatcgct gatcttggag gctgcccgcc gcacatgttt      60
tataaaagcg ctgctgaaaa atataacctg gtcagcttta ttccaagacc ttttgcaatt     120
acagcctccc atgcagcatt gattgaaaaa tactcggtcg cggtcataaa agataaagac     180
tattttaaga gtttagctga ttttgaacac cctgattcca tttattgggc gcatgaagat     240
cataacaagc tgaggaaga ggtcgtcgag caaatcgtca aggttgccga aatgtttggg     300
gcggatgcca tcacaacaaa cgcggaatta ttcgtggctc cgatggcgaa agcctgtgaa     360
cgtctgggct tgagaggtgc cggcgtgcag gcagccgaaa atgccagaga taaaaataaa     420
atgagggacg cttttaataa ggccggagtc aaatcgatca aaaacaaacg agtcacaact     480
cttgaagatt tccgtgctgc tcttgaagag atcggcacac ctcttatctt aaagcctaca     540
```

```
tacttagcga gttctatcgg tgtaacgctg attacggaca ctgagacggc agaagatgaa      600
tttaacagag tcaatgacta tctgaaatca attaacgtgc caaaggcggt tacgtttgaa      660
gcgccgttta tcgctgaaga attttttacag ggtgagtacg gagactggta tcaaacagaa     720
```
(Note: line 720 as printed: `gcgccgttta tcgctgaaga atttttacag ggtgagtacg gagactggta tcaaacagaa`)

```
gggtactccg actatatcag tatagaaggc atcatggctg acggtgagta tttcccgatc      780
gccattcatg ataaaacgcc gcaaatcggg tttacagaga catcccacat tacgccgtcc      840
attctggatg aagaggcaaa aagaaaatt gtcgaagctg ccaaaaaggc aaatgaaggg       900
cttggactgc aaaattgcgc aacacataca gagatcaagc taatgaaaaa cagagaaccg      960
ggtttaatag agtcggcagc cagatttgcc ggctggaata tgatccccaa tattaaaaag    1020
gtctttggcc ttgatatggc gcaattatta ttagatgtcc tctgtttcgg aaaagacgcc    1080
gatctgccgg acggattatt ggatcaagag ccttattatg ttgccgactg ccgcttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc tttttcggcc    1260
gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                            1419
```

<210> SEQ ID NO 31
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108Q/I112V/H378K)

<400> SEQUENCE: 31

```
atggagagaa aaacagtatt ggtcatcgct gatcttggag gctgcccgcc gcacatgttt      60
tataaaagcg ctgctgaaaa atataacctg gtcagcttta ttccaagacc ttttgcaatt     120
acagcctccc atgcagcatt gattgaaaaa tactcggtcg cggtcataaa agataaagac     180
tattttaaga gttagctga ttttgaacac cctgattcca tttattgggc gcatgaagat      240
```
(line 240 as printed: `tattttaaga gttagctga ttttgaacac cctgattcca tttattgggc gcatgaagat`)

```
cataacaagc ctgaggaaga ggtcgtcgag caaatcgtca aggttgccga atgtttggg      300 gcggatgcca tcacaacaaa ccaggaatta ttcgtggctc cgatggcgaa agcctgtgaa      360
cgtctgggct tgagaggtgc cggcgtgcag gcagccgaaa atgccagaga taaaaataaa      420
atgagggacg cttttaataa ggccggagtc aaatcgatca aaaacaaacg agtcacaact      480
cttgaagatt tccgtgctgc tcttgaagag atcggcacac ctcttatctt aaagcctaca      540
tacttagcga gttctatcgg tgtaacgctg attacggaca ctgagacggc agaagatgaa      600
tttaacagag tcaatgacta tctgaaatca attaacgtgc caaaggcggt tacgtttgaa      660
gcgccgttta tcgctgaaga attttttacag ggtgagtacg gagactggta tcaaacagaa    720
gggtactccg actatatcag tatagaaggc atcatggctg acggtgagta tttcccgatc     780
gccattcatg ataaaacgcc gcaaatcggg tttacagaga catcccacat tacgccgtcc     840
attctggatg aagaggcaaa aagaaaatt gtcgaagctg ccaaaaaggc aaatgaaggg      900
cttggactgc aaaattgcgc aacacataca gagatcaagc taatgaaaaa cagagaaccg     960
ggtttaatag agtcggcagc cagatttgcc ggctggaata tgatccccaa tattaaaaag   1020
gtctttggcc ttgatatggc gcaattatta ttagatgtcc tctgtttcgg aaaagacgcc   1080
gatctgccgg acggattatt ggatcaagag ccttattatg ttgccgactg caaattgtac   1140
```

```
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc     1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                           1419
```

<210> SEQ ID NO 32
<211> LENGTH: 1419
<212> TYPE: DNA
<213> ORGANISM: Bacillus subtilis
<220> FEATURE:
<221> NAME/KEY: misc_feature
<223> OTHER INFORMATION: YwfE (mutant type: N108Q/I112V/H378R)

<400> SEQUENCE: 32

```
atggagagaa aaacagtatt ggtcatcgct gatcttggag gctgcccgcc gcacatgttt    60
tataaaagcg ctgctgaaaa atataacctg gtcagcttta ttccaagacc ttttgcaatt    120
acagcctccc atgcagcatt gattgaaaaa tactcggtcg cggtcataaa agataaagac    180 tatttttaaga gtttagctga ttttgaacac cctgattcca tttattgggc gcatgaagat    240
cataacaagc tgaggaaga ggtcgtcgag caaatcgtca aggttgccga aatgtttggg     300
gcggatgcca tcacaacaaa ccaggaatta ttcgtggctc cgatggcgaa agcctgtgaa    360
cgtctgggct tgagaggtgc cggcgtgcag gcagccgaaa atgccagaga taaaaataaa    420
atgagggacg cttttaataa ggccggagtc aaatcgatca aaaacaaacg agtcacaact    480
cttgaagatt tccgtgctgc tcttgaagag atcggcacac ctcttatctt aaagcctaca    540
tacttagcga gttctatcgg tgtaacgctg attacggaca ctgagacggc agaagatgaa    600
tttaacagag tcaatgacta tctgaaatca attaacgtgc aaaggcggt tacgtttgaa    660 gcgccgttta cgctgaagag atttttacag ggtgagtacg gagactggta tcaaacagaa    720
gggtactccg actatatcag tatagaaggc atcatggctg acggtgagta tttcccgatc    780
gccattcatg ataaaacgcc gcaaatcggg tttacagaga catcccacat tacgccgtcc    840
attctggatg aagaggcaaa aaagaaaatt gtcgaagctg ccaaaaaggc aaatgaaggg    900
cttggactgc aaaattgcgc aacacataca gagatcaagc taatgaaaaa cagagaaccg    960
ggtttaatag agtcggcagc cagatttgcc ggctggaata tgatccccaa tattaaaaag    1020
gtctttggcc ttgatatggc gcaattatta ttagatgtcc tctgtttcgg aaaagacgcc    1080
gatctgccgg acggattatt ggatcaagag ccttattatg ttgccgactg ccgcttgtac    1140
ccgcagcatt tcaaacaaaa tggccaaatt cctgaaactg ctgaggattt ggtcattgaa    1200
gcgatcgata ttccggacgg gcttttaaaa ggggatactg aaatcgtttc ttttcggcc     1260 gcagcaccag gcacttcagt tgatttgaca ttgtttgaag ctttcaattc cattgctgca    1320
tttgaactga aaggcagtaa ttcacaggat gtggctgaat caatcagaca aattcagcag    1380
catgcgaagc tgacggcaaa gtatgtgctg ccagtatga                           1419
```

<210> SEQ ID NO 33
<211> LENGTH: 33
<212> TYPE: DNA
<213> ORGANISM: Artificial Sequence
<220> FEATURE:
<223> OTHER INFORMATION: N108A_sense

<400> SEQUENCE: 33
acaaacgcgg aattattcat tgctccgatg gcg            33

<210> SEQ ID NO 34
<211> LENGTH: 33
<212> TYPE: DNA
<213> ORGANISM: Artificial Sequence
<220> FEATURE:
<223> OTHER INFORMATION: N108A_antisense
<400> SEQUENCE: 34
taattccgcg tttgttgtga tggcatccgc ccc            33

<210> SEQ ID NO 35
<211> LENGTH: 33
<212> TYPE: DNA
<213> ORGANISM: Artificial Sequence
<220> FEATURE:
<223> OTHER INFORMATION: N108E_sense
<400> SEQUENCE: 35
acaaacgaag aattattcat tgctccgatg gcg            33

<210> SEQ ID NO 36
<211> LENGTH: 33
<212> TYPE: DNA
<213> ORGANISM: Artificial Sequence
<220> FEATURE:
<223> OTHER INFORMATION: N108E_antisense
<400> SEQUENCE: 36
taattcttcg tttgttgtga tggcatccgc ccc            33

<210> SEQ ID NO 37
<211> LENGTH: 33
<212> TYPE: DNA
<213> ORGANISM: Artificial Sequence
<220> FEATURE:
<223> OTHER INFORMATION: N108Q_sense
<400> SEQUENCE: 37
acaaaccagg aattattcat tgctccgatg gcg            33

<210> SEQ ID NO 38
<211> LENGTH: 33
<212> TYPE: DNA
<213> ORGANISM: Artificial Sequence
<220> FEATURE:
<223> OTHER INFORMATION: N108Q_antisense
<400> SEQUENCE: 38
taattcctgg tttgttgtga tggcatccgc ccc            33

<210> SEQ ID NO 39
<211> LENGTH: 33
<212> TYPE: DNA
<213> ORGANISM: Artificial Sequence
<220> FEATURE:
<223> OTHER INFORMATION: I112V_sense
<400> SEQUENCE: 39
ttattcgtgg ctccgatggc gaaagcctgt gaa            33

<210> SEQ ID NO 40
<211> LENGTH: 33
<212> TYPE: DNA

<210> SEQ ID NO 41
<211> LENGTH: 33
<212> TYPE: DNA
<213> ORGANISM: Artificial Sequence
<220> FEATURE:
<223> OTHER INFORMATION: I112V _antisense

<400> SEQUENCE: 40
cggagccacg aataattcat tgtttgttgt gat          33

<210> SEQ ID NO 41
<211> LENGTH: 33
<212> TYPE: DNA
<213> ORGANISM: Artificial Sequence
<220> FEATURE:
<223> OTHER INFORMATION: H378K_sense

<400> SEQUENCE: 41
gactgcaaat tgtacccgca gcatttcaaa caa          33

<210> SEQ ID NO 42
<211> LENGTH: 33
<212> TYPE: DNA
<213> ORGANISM: Artificial Sequence
<220> FEATURE:
<223> OTHER INFORMATION: H378K_antisense

<400> SEQUENCE: 42
gtacaatttg cagtcggcaa cataataagg ctc          33

<210> SEQ ID NO 43
<211> LENGTH: 33
<212> TYPE: DNA
<213> ORGANISM: Artificial Sequence
<220> FEATURE:
<223> OTHER INFORMATION: H378R_sense

<400> SEQUENCE: 43
gactgccgct tgtacccgca gcatttcaaa caa          33

<210> SEQ ID NO 44
<211> LENGTH: 33
<212> TYPE: DNA
<213> ORGANISM: Artificial Sequence
<220> FEATURE:
<223> OTHER INFORMATION: H378R_antisense

<400> SEQUENCE: 44
gtacaagcgg cagtcggcaa cataataagg ctc          33